US010052267B2

(12) United States Patent
Johnston et al.

(10) Patent No.: US 10,052,267 B2
(45) Date of Patent: *Aug. 21, 2018

(54) TOPICAL GLYCOPYRROLATE FORMULATIONS

(71) Applicant: ROSE U, LLC, Palo Alto, CA (US)

(72) Inventors: Michael Johnston, Yarraville (AU); Robert James Houlden, Kilsyth (AU)

(73) Assignee: ROSE U, LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/662,166

(22) Filed: Jul. 27, 2017

(65) Prior Publication Data
US 2018/0008517 A1 Jan. 11, 2018

Related U.S. Application Data

(63) Continuation of application No. 14/084,010, filed on Nov. 19, 2013, now Pat. No. 9,744,105, which is a continuation of application No. 12/738,168, filed as application No. PCT/US2008/011907 on Oct. 17, 2008, now Pat. No. 8,618,160.

(60) Provisional application No. 60/960,887, filed on Oct. 18, 2007.

(51) Int. Cl.
| A61K 9/00 | (2006.01) |
| A61K 8/02 | (2006.01) |
| A61K 47/10 | (2017.01) |
| A61K 47/32 | (2006.01) |
| A61K 31/40 | (2006.01) |
| A61Q 15/00 | (2006.01) |
| A61K 8/49 | (2006.01) |

(52) U.S. Cl.
CPC ......... *A61K 8/0208* (2013.01); *A61K 8/4913* (2013.01); *A61K 9/0014* (2013.01); *A61K 31/40* (2013.01); *A61K 47/10* (2013.01); *A61K 47/32* (2013.01); *A61Q 15/00* (2013.01)

(58) Field of Classification Search
None
See application file for complete search history.

(56) References Cited

U.S. PATENT DOCUMENTS

| 2,118,566 | A | 5/1938 | Miles |
| 3,312,709 | A | 4/1967 | MacMillan |
| 3,557,125 | A | 1/1971 | Zeile et al. |
| 3,767,786 | A | 10/1973 | MacMillan |
| 4,355,020 | A | 10/1982 | Kuy |
| 4,415,551 | A | 11/1983 | Fang |
| 4,824,676 | A | 4/1989 | Bodor |
| 4,891,227 | A | 1/1990 | Thaman et al. |
| 5,403,588 | A | 4/1995 | Santa Ana, Jr. |
| 5,648,083 | A | 7/1997 | Blieszner et al. |
| 5,962,505 | A | 10/1999 | Bobrove et al. |
| 6,211,250 | B1 | 4/2001 | Tomlinson et al. |
| 6,433,003 | B1 | 8/2002 | Bobrove et al. |
| 6,446,795 | B1 | 9/2002 | Allen et al. |
| 7,060,289 | B2 | 6/2006 | Wassenaar |
| 8,618,160 | B2 | 12/2013 | Johnston et al. |
| 9,744,105 | B2 | 8/2017 | Johnston et al. |
| 2003/0115837 | A1 | 6/2003 | Zimmer et al. |
| 2006/0165765 | A1 | 7/2006 | Wassenaar |
| 2006/0211729 | A1 | 9/2006 | Fyrnys et al. |
| 2009/0208437 | A1 | 8/2009 | Woehrmann et al. |

FOREIGN PATENT DOCUMENTS

| AU | 2002302222 | 11/2003 |
| AU | 2014203072 B2 | 7/2014 |
| CA | 2384922 | 11/2003 |
| EP | 0342054 A2 | 11/1989 |
| ES | 2118053 | 3/1999 |
| GB | 1080960 A | 8/1967 |
| GB | 2018713 A | 10/1979 |
| WO | WO 93/25186 A1 | 12/1993 |
| WO | WO 03/092641 A1 | 11/2003 |
| WO | WO 2006/069998 A2 | 7/2006 |
| WO | PCT/US2008/011907 | 4/2009 |

OTHER PUBLICATIONS

1st Statutory Declaration of Jim O. Onishi dated Feb. 22, 2017; 2 pages.
2nd Statutory Declaration of Jim O. Onishi dated Feb. 24, 2017; 2 pages.
Attwood, "Micellar and Nonmicellar Association of Antiacetylcholine Drugs in Aqueous Solution", *The Journal of Physical Chemistry*, (1976), vol. 80, No. 18, pp. 1984-1987.
Benohanian et al., "Localized Hyperhidrosis Treated with Aluminum Chloride in a Salicylic Acid Gel Base", *International J. Dermatology*, (1996), vol. 37, pp. 701-708.
Communication pursuant to Article 94(3) EPC dated Nov. 23, 2016 for EP application No. 08839892.0, 6 pages.
Communication under Rule 71(3) EPC in the EP application No. 08839892.0 dated Oct. 16, 2017, 7 pages.
Declarations (under 37 C.F.R. 1.132) of Dipen Kalaria signed on Jun. 29, 2009 and Nov. 12, 2010, 50 pages.
Examination Report for Canadian patent application No. 2,702,830 dated May 20, 2015; 4 pages.
Examination report on voluntary amendments dated Nov. 7, 2017 for AU application No. 2014203072; 2 pages.
Exhibit JYO-1 referred to in the Statutory Declaration of Dr. Jim Y. Onishi made this Feb. 22, 2017, Request for re-examination of a complete specification dated Dec. 15, 2014, 25 pages.

(Continued)

*Primary Examiner* — James W Rogers
(74) *Attorney, Agent, or Firm* — Squire Patton Boggs (US) LLP

(57) ABSTRACT

Individually packaged topical formulations comprising about 0.25 to about 6% w/w of glycopyrrolate for the treatment of hyperhidrosis, wherein said wipe is contained within a pouch resistant to leakage. The formulations may further comprise ethanol, a buffering agent and water. In addition, the formulations may further comprise a polymer system comprising a hydrophobic polymer in combination with a hydrophilic polymer.

20 Claims, 13 Drawing Sheets

(56) References Cited

OTHER PUBLICATIONS

Exhibit JYO-4 referred to in the Statutory Declaration of Dr. Jim Y. Onishi made this Feb. 24, 2017, Patent Examination Report, dated Jan. 8, 2013, 4 pages.
Exhibit JYO-5 referred to in the Statutory Declaration of Dr. Jim Y. Onishi made this Feb. 24, 2017, Agent's letter to AU Examiner dated Jan. 6, 2014, 21 pages.
Exhibit JYO-6 referred to in the Statutory Declaration of Dr. Jim Y. Onishi made this Feb. 24, 2017, Patent Examination Report, dated May 18, 2015, 4 pages.
Exhibit WW-31 dated Feb. 10, 2017 referred to in the Statutory Declaration of Dr. Willem Wassenaar, Notification of a Requisition by the CA examiner for application No. 2,702,830 dated Jul. 30, 2014, 3 pages.
Exhibit WW-32 dated Feb. 10, 2017 referred to in the Statutory Declaration of Dr. Willem Wassenaar, Response to Official Action dated Jan. 29, 2015, 17 pages.
Exhibit WW-33 dated Feb. 10, 2017 referred to in the Statutory Declaration of Dr. Willem Wassenaar, Notification of a Requisition by the CA examiner for application No. 2,702,830 dated May 20, 2015, 5 pages.
Exhibit WW-34 dated Feb. 17, 2017 referred to in the Statutory Declaration of Dr. Willem Wassenaar, Non-Final office action of U.S. Appl. No. 14/084,010 dated Jul. 15, 2016, 10 pages.
Exhibit JBB-02 referred to in the Statutory Declaration of Jonathan B. Baell made this Jul. 10, 2015, for AU Patent No. 2008314628, 2 pages.
Extended European Search Report for EP application No. 08839892.0 dated Jan. 5, 2016; 9 pages.
Hays et al., "The Frey Syndrome: A Simple, Effective Treatment", *Otolaryngol Head Neck Surg.*, (Jul.-Aug. 1982), vol. 90, pp. 419-425.
Hays, "The Frey Syndrome: A Review and Double Blind Evaluation of the Topical Use of a New Anticholinergic Agent", *The Laryngoscope*, (1978), vol. 88, pp. 1796-1824.
Ingallinera et al., "Compatibility of Glycopyrrolate Injection with Commonly Used Infusion Solutions and Additives", *American J. Hosp. Pharm.*, (Apr. 1979), vol. 36, pp. 508-510.
International search report dated Dec. 16, 2008, and International preliminary report on patentability dated Apr. 20, 2010 for PCT/US2008/011907 (WO2009/051818), 8 pages.
Martindale, "The Complete Drug Reference", 32nd Edition published in 1999 by the *Pharmaceutical Press*; 4 pages.
Notice of Allowance for Canadian application No. 2,702,830 dated Dec. 19, 2016; 1 page.
Official Letter to the Australian Patent Office dated Nov. 11, 2015 together Statutory Declarations of Adam Watkinson dated Nov. 9, 2015 with Exhibit "AW-01" and Christopher J. Burns dated Nov. 11, 2015 with Exhibit "CJB-01"; 39 pages.
Opponent (Purepharm Inc.) Comments dated Nov. 3, 2017 for AU Patent Application No. 2014203072, 10 pages.
Opponent (Purepharm Inc.) Comments dated Sep. 26, 2017 for AU Patent Application No. 2014203072, 5 pages.
Patent Oppositions for AU Patent Application No. 2014203072 dated Dec. 15, 2016, 7 pages.
Physicians Desk Reference, 48 Edition, Medical Economics Co., publisher, Montvale, NJ, 1994; 1 page.
Re-examination—Patent Oppositions by Purepharm Inc. for AU patent No. 2008314628 dated Mar. 10, 2016, 169 pages.
Re-examination—Patent Oppositions by Purepharm Inc. for AU patent No. 2008314628 dated Mar. 21, 2016, Additional information to support Re-examination filed on Mar. 10, 2016; 8 pages.
Re-Examination Report—Standard Patent for AU Patent Application No. 2008314628 dated Feb. 9, 2015, 3 pages.
Re-Examination Report—Standard Patent for AU Patent Application No. 2008314628 dated Sep. 11, 2015, 3 pages.
Re-Examination Report—Standard Patent for AU Patent Application No. 2008314628 dated Nov. 26, 2015, 4 pages.
Re-Examination Report—Standard Patent for AU Patent No. 2008314628 dated Apr. 14, 2016, 4 pages.
Remington's Pharmaceutical Sciences, 13th Edition published by the Mack Publishing Company in 1965, Chapter 17, pp. 242-247.
Response to Oppositions and Hearings for Australian Patent Application No. 2014203072 filed on Sep. 6, 2017, 17 pages.
Seukeran et al., "The use of topical glycopyrrolate in the treatment of hyperhidrosis", *Clinical and Experimental Dermatology*, 1998, vol. 23, pp. 204-205.
Statement of Grounds and Particulars of Opposition for AU application No. 2014203072 lodged by Purepharm Inc. on Nov. 25, 2016, 49 pages.
Statutory Declaration of Jonathan Baell dated Feb. 23, 2017; 5 pages.
Statutory Declaration of Jonathan Baell dated Jul. 10, 2015, with Exhibit JBB-01; 7 pages.
Statutory Declaration of Willem Wassenaar dated Feb. 10, 2017; 46 pages.
Statutory Declaration of Jim O. Onishi for AU Patent Application No. 2014203072 dated Jun. 29, 2017, with Exhibits JYO-10, JYO-11, JYO-12, 24 pages.
The United States Trade Commission Ruling NY 807493 dated Mar. 30, 1995; 3 pages.
The United States Pharmacopeia, The National Formulary, USP 23, NF 18, 1995, 2 pages.
The United States Trade Commission Rulings and Hormonized Tariff Schedule, HQ 966800 dated Feb. 3, 2004, 4 pages.
Third Party Observation Against EP2200550 (application No. 08839892.0) dated Feb. 2, 2015; 79 pages.
Third Party Observation Against EP2200550 (application No. 08839892.0) dated Mar. 23, 2017, 10 pages.
Third Party Re-Examination by Purepharm Inc. for AU Patent No. 2008314628 dated Jul. 30, 2015; 81 pages.
Third Party Re-Examination by Purepharm Inc. for AU patent No. 2008314628 dated Dec. 19, 2014; 25 pages.
Third Party Submission Under 37 CFR 1.290 in U.S. Appl. No. 14/084,010 (now U.S. Pat. No. 9,744,105), filed on Dec. 30, 2014, 25 pages.
Van Slyke Donald, "On the Measurement of Buffer Values and on the Relationship of Buffer Value to the Dis-Sociation Constant of the Buffer and the Concentration and Reaction of the Buffer Solution", pp. J. Biol. Chem., 1922, vol. 52, pp. 525-570.

FIGURE 1A. Packages

FIGURE 1B. Packaging interactions

FIGURE 2
FIGURE 2A
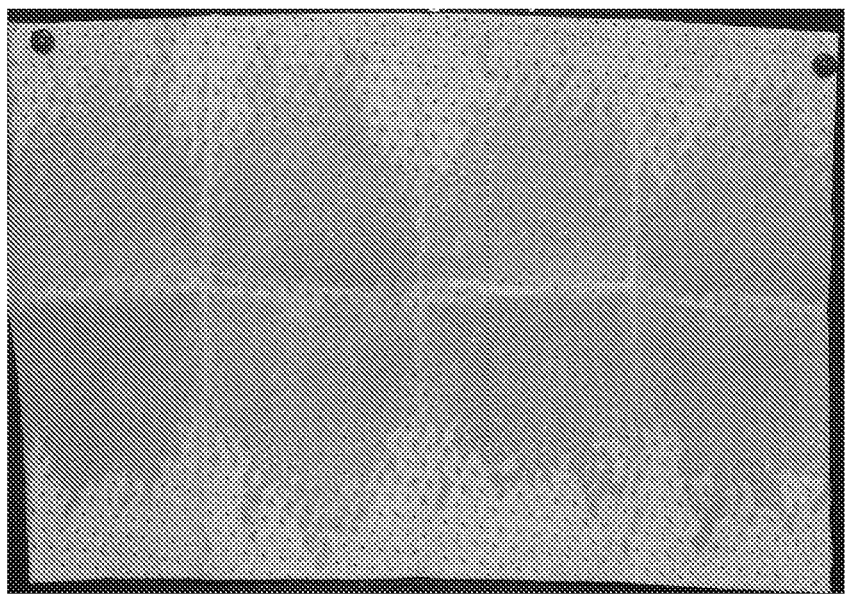
FIGURE 2B
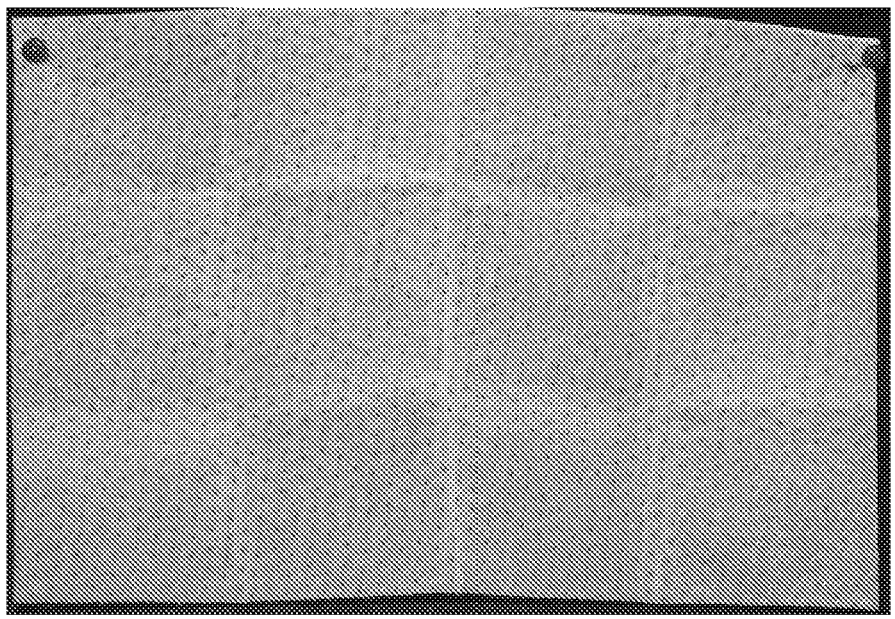

FIGURE 3A. Dose delivery of the Ethanol Solution placebo from two wipe sizes

FIGURE 3B. Dose delivery of the Ethanol Solution placebo from two wipe sizes and two wipe thicknesses.

Saturation Solubility of Glycopyrrolate at 5'C pH of Base and Wipe solutions versus buffer ratio for ES (top) and EPX (bottom) formulations Moist robustness results. API (Active Pharmaceutical Ingredient) remaining after wiping a dried film on a glass slide with a weighted damp cloth (n=2 for each result)

Photos of dried films bent to 4.7 cm diameter, 30°C/75% RH: Top -with Povidone K90, Bottom - No Povidone K-90

Some of the cracks in the film

Water release from dried films of the base solution

Figure 11A Average HDSS For Ethanol Solutions

Figure 11B Average HDSS For EPX formulations

Figure 12A Gravimetric analysis for Ethanol Solutions

Figure 12B Gravimetric analysis for EPX formulations

TOPICAL GLYCOPYRROLATE FORMULATIONS

This application is a continuation application of U.S. application Ser. No. 14/084,010 filed Nov. 19, 2013, now U.S. Pat. No. 9,744,105, which is a continuation application of U.S. application Ser. No. 12/738,168 filed Jun. 23, 2010, now U.S. Pat. No. 8,618,160, which is a 371 of PCT/US08/11907 filed on Oct. 17, 2008 which claims priority to U.S. Provisional Application No. 60/960,887 filed Oct. 18, 2007. The disclosures of the above referenced applications are incorporated by reference herein in their entireties.

FIELD OF THE INVENTION

The present invention relates to topical formulations comprising a glycopyrrolate compound. In particular, the present invention relates to individually packaged topical formulations comprising a glycopyrrolate compound and methods for preparing the same. These formulations are particularly used to alleviate hyperhidrosis in a mammal who suffers from the symptom.

BACKGROUND OF THE INVENTION

Hyperhidrosis is a disorder characterized by excessive sweating, namely sweating in excess of that required for the regulation of body temperature, that occurs in up to 1% of the population, with women being the predominant group affected by this condition. The excessive sweating associated with hyperhidrosis can occur in the hands (palmar hyperhidrosis), in the armpits (axillary hyperhidrosis), or in the feet (plantar hyperhidrosis). The underlying cause for primary hyperhidrosis, i.e., idiopathic hyperhidrosis, is not completely understood, but it is widely believed that an overactive sympathetic nervous system is involved, as it is known that sweating is generally under the control of the sympathetic nervous system. Secondary hyperhidrosis can be distinguished from primary hyperhidrosis as being due to a disorder of the thyroid or pituitary gland, diabetes mellitus, tumors, gout, menopause, or certain drugs.

Regardless of its causation, many patients afflicted with hyperhidrosis experience a distinct reduction in quality of life. Sufferers may feel a loss of control because perspiration can take place independent of temperature and sometimes emotional state. However, anxiety can frequently exacerbate the situation in many sufferers. Other factors are known to play a role; for example, certain foods and drinks, nicotine, caffeine, and smells can also trigger a response.

Hyperhidrosis can have a severe impact on quality of life and can interfere with the performance of routine activities. Perhaps one of the most severe consequences of hyperhidrosis is observed in work and social contexts. Patients with palmar hyperhidrosis have wet, moist hands that sometimes interfere with grasping objects. Many patients with palmar hyperhidrosis also consider it difficult to shake hands, as a handshake may leave the other person's palm very moist, a sensation most people find unpleasant. Those who suffer from axillary hyperhidrosis sweat profusely from their underarms causing them to stain their clothes shortly after they dress. These manifestations of hyperhidrosis place sufferers of this condition at a severe disadvantage in many social and professional situations.

In addition, the excessive sweating associated with hyperhidrosis impedes the performance of many routine activities. Activities such as driving, taking tests and simply grasping objects are severely hampered by sweaty hands. In addition, many careers and social situations present challenges for hyperhidrosis sufferers. For example, excessive sweating of the hands can be a debilitating condition because an individual's hands are much more exposed in social and professional activities than any other part of the body. Thus, many individuals with this condition may feel limited in their choice of professions and social interactions. For example, such individuals may be unable to manipulate materials sensitive to humidity (paper etc.) and are reluctant to shake hands. Other patients choose to minimize or avoid social contact.

A number of treatments are currently available for the treatment of hyperhidrosis; however, all of the treatments involve particular disadvantages for some patients.

A surgical procedure known as endoscopic thoracic sympathectomy or ETS is available in which selected sympathetic nerves or nerve ganglia in the chest are either cut or burned, thus completely destroying their ability to transmit impulses. Alternatively, these nerves can be clamped, thus affording the possibility of reversal of the procedure. However, this procedure often causes anhidrosis from the mid-chest upwards, which itself is a disturbing condition for many patients. Other major drawbacks to the procedure include thermoregulatory dysfunction (Goldstein, 2005), lowered fear and alertness (Teleranta, Pohjavaara, et al 2003, 2004) and the overwhelming incidence of compensatory hyperhidrosis. Many patients find the resultant compensatory hyperhidrosis to be worse than the initial condition. Moreover, the general risks normally associated with chest surgery are attendant with this procedure.

Another surgical treatment is sweat gland suction, which is a procedure modified from liposuction. Performed on an out-patient basis with only local anesthesia, the sweat glands are permanently removed. To perform this procedure, the sweat glands and armpits are first softened and anaesthetized with a special solution. After a short period, the sweat glands can then be removed by aspiration in a manner similar to liposuction.

Antiperspirants are another course of treatment for hyperhidrosis. The most effective antiperspirant agent appears to be 20 to 25% aluminum chloride in 70 to 90% alcohol, applied in the evening, 2 to 3 times/week. Aluminum chloride is the active agent found in a number of common antiperspirant products, including Drysol®, Maxim®, Odaban®, and Driclor®. However, hyperhidrosis sufferers generally need a much higher concentration than is found in ordinary commercially available products. Moreover, even a 15% or higher aluminum chloride solution usually takes about a week of nightly use to stop the sweating, with a follow-up of one or two nightly applications per week required to maintain the results. While aluminum chloride solutions can be effective, some people cannot tolerate the irritation that this agent causes in some users. Also, the solution is usually not effective for palmar (hand) and plantar (foot) hyperhidrosis.

Injections of the botulinum toxin (Botulinum toxin type A (trademarked as Botox®)) have also been used to disable the sweat glands. The effects can last from 4 to 9 months depending on the site of injections. For some patients, proper anesthesia may be required for the reduction of pain associated with injections to the hand and foot. Use of the procedure to treat underarm sweating has been approved by the FDA. However, this toxin is one of the most lethal poisons known, interfering with the effect of the neurotransmitter acetylcholine at synapses and potentially leading to progressive paralysis of all muscles in the body, including the respiratory muscles at higher doses than that used for treatment of hyperhidrosis. Another drawback is the cost of this treatment which has to be repeated at regular intervals.

Another method of treatment is iontophoresis which consists of the application of low intensity electric current (15-18 mA), supplied by a D/C generator, to the palms and/or soles immersed in an electrolyte solution. As the low current passes through an affected area, the minerals in the water clog the sweat glands, limiting the amount of sweat released. The procedure must be repeated regularly, initially in 20 minute sessions several times/week, with a gradual lengthening of the interval between treatments to 1 to 2 weeks. The results may vary; many patients, suffering from light or moderate hyperhidrosis, are satisfied with the method, while others may consider this procedure too time-consuming or inefficient, and comparably expensive. Moreover, this procedure is difficult to apply to the axillary area, and is not suitable for use in diffuse hyperhidrosis of the face or the trunk/thigh region. Also, this procedure has been found to be painful for some patients.

There are several drugs currently in use with varying degrees of success. A class of anticholinergic drugs has been shown to reduce hyperhidrosis. These drugs include Ditropan® (generic name: oxybutynin), which for some patients causes an unacceptable amount of drowsiness and dry-mouth; other less effective anticholinergic agents have also been used, including propantheline bromide (Probanthine®) and benztropine (Cogentin®). A different class of drugs which function as beta-blockers has also been tried, but these agents do not seem to be nearly as effective.

Glycopyrrolate is a quaternary amine of the muscarinic anticholinergic group. Glycopyrrolate has been used in the treatment of a variety of conditions including diarrhea (U.S. Pat. Nos. 6,214,792 and 5,919,760), urinary incontinence (U.S. Pat. Nos. 6,204,285 and 6,063,808), and anxiety (U.S. Pat. No. 5,525,347). Additionally, U.S. Pat. No. 5,976,499 discloses a method for diagnosing cystic fibrosis in a patient by, in part, stimulating sweat production through the injection of a glycopyrrolate solution into a patient.

Glycopyrrolate has also been previously used for the treatment of hyperhidrosis on an off-label basis, but as discussed below, these applications of glycopyrrolate lack the advantages of the present invention.

Abell et al., *British Journal of dermatology* 91: 87-91 (1974), discloses a method of treatment of hyperhidrosis including the use of glycopyrrolate in solutions for iontophoresis. A 0.5% aqueous solution of glycopyrrolate applied to the scalp and forehead for the treatment of hyperhidrosis has also been described in Seukeran et al., *Clinical and Experimental Dermatology*, 23: 204-205 (1998).

U.S. Pat. No. 6,433,003 to Bobrove discloses the topical use of about 0.25 to about 6% glycopyrrolate in the form of a lotion for the treatment of hyperhidrosis.

U.S. Pat. No. 7,060,289 to Wassenaar discloses a sealable container containing 30 rayon/polypropylene pads comprising 2% glycopyrrolate. This formulation of glycopyrrolate is not conducive to ease of use and ready portability, for instance, in a purse or briefcase or in an individual's pocket, as such a large container would be bulky and awkward to carry around on a routine basis. Furthermore, repeated opening of the sealable container of U.S. Pat. No. 7,060,289 would result, over time, in evaporation of the ethanol solution used in the glycopyrrolate formulation and a subsequent change in the concentration of the glycopyrrolate. Furthermore, continual exposure of the glycopyrrolate formulation of U.S. Pat. No. 7,060,289 to the air would also result, over time, in degradation of the active ingredient.

Given the drawbacks in terms of effectiveness and convenience of the presently available forms of treatment for hyperhidrosis, there remains a need for an effective, convenient, and easy to use formulation for the reduction of sweating caused in everyday situations that may exacerbate hyperhidrosis in sufferers of this condition.

BRIEF SUMMARY OF THE INVENTION

To arrive at formulations of glycopyrrolate that meet the above criteria of effectiveness, ease of use, and ready portability, the present inventors have devised an individually packaged wipe of glycopyrrolate that is easy to carry and use on a moment's notice as required. The present inventors have overcome problems associated with glycopyrrolate formulating and packaging, such as the ability to maintain high levels of the active agent upon prolonged storage, proper maintenance of an effective pH of the formulations, and the corrosiveness of formulations to many packaging materials that are commonly used for individual packaging of items such as wipes. As a consequence, the present inventors provide such topical formulations as needed for the treatment of hyperhidrosis.

The present invention provides an effective, convenient, and easy to carry formulation of glycopyrrolate for the treatment of hyperhidrosis that may be used in a variety of situations where triggers of the excessive sweating associated with hyperhidrosis are likely to occur (e.g., before social occasions, speaking engagements, job interviews, and the like), as well as for excessive sweating that may result from the performance of ordinary everyday activities.

One aspect of the present invention relates to an individually packaged wipe for the treatment of hyperhidrosis comprising glycopyrrolate at about 0.25 to about 6% w/w, wherein said wipe is contained within a pouch resistant to leakage. The glycopyrrolate according to this aspect degrades by less than 1% when stored at 0 to 25° C. for 1 month, 2 months, 6 months, or 1 year.

In an embodiment of this aspect, the present invention relates to an individually packaged wipe for the treatment of hyperhidrosis comprising glycopyrrolate at about 0.25 to about 6% w/w, wherein said wipe is contained within a pouch resistant to leakage and the pouch comprises an inner lining of linear low density polyethylene (LLDPE).

Another aspect of the present invention relates to an individually packaged wipe for the treatment of hyperhidrosis comprising glycopyrrolate at about 0.25 to about 6% w/w, wherein said wipe is contained within a pouch resistant to leakage, and further comprising an alcohol, a buffering agent and water. Ethanol is preferred for the alcohol. The glycopyrrolate according to this aspect degrades by less than 1% when stored at 0 to 25° C. for 1 month, 2 months, 6 months, or 1 year.

In an embodiment of this aspect, the present invention relates to an individually packaged wipe for the treatment of hyperhidrosis comprising glycopyrrolate at about 0.25 to about 6% w/w, an alcohol, a buffering agent and water, wherein said wipe is contained within a pouch resistant to leakage and the buffering agent comprises citric acid and sodium citrate to maintain a pH of about 3.5 to about 6. In another embodiment, the alcohol is ethanol and the buffering agent may comprise citric acid and tromethamine to maintain a pH of about 3.5 to about 6. The pH is preferably maintained at about 4±0.5, or about 4 to about 5, more preferably at about 4.5.

In another embodiment of this aspect, the present invention relates to an individually packaged wipe for the treatment of hyperhidrosis comprising glycopyrrolate at about 0.25 to about 6% w/w, an alcohol, a buffering agent and water, wherein said wipe is contained within a pouch resistant to leakage and the ethanol and water is in the weight ratio of about 40:60 to about 60:40. The alcohol is preferably ethanol and the weight ratio of ethanol to water is preferably about 60:40.

In another embodiment of this aspect, the present invention relates to an individually packaged wipe for the treatment of hyperhidrosis comprising glycopyrrolate at about 0.25 to about 6% w/w, an alcohol, a buffering agent and water, wherein said wipe is contained within a pouch resistant to leakage and wherein the alcohol, preferably ethanol, is present in the amount of about 53.7 to about 57.3% w/w, the buffering agent is in the amount of about 0.2 to about 0.5% w/w and the water is added to 100% w/w.

Another aspect of the present invention relates to an individually packaged wipe for the treatment of hyperhidrosis comprising glycopyrrolate at about 0.25 to about 6% w/w, wherein said wipe is contained within a pouch resistant to leakage, which further comprises an alcohol, a buffering agent, water, a polymer system comprising a hydrophobic polymer in combination with a hydrophilic polymer. The alcohol is preferably ethanol and the polymer system preferably comprises a polyvinyl pyrrolidone and a butyl ester of polyvinylmethylether/maleic anhydride copolymer. The glycopyrrolate according to the present invention of this aspect degrades by less than 1% when stored at 0 to 25° C. for 1 month, 2 months, 6 months, or 1 year.

In an embodiment of this aspect, the present invention relates to an individually packaged wipe for the treatment of hyperhidrosis comprising glycopyrrolate at about 0.25 to about 6% w/w, wherein said wipe is contained within a pouch resistant to leakage, which further comprises ethanol, a buffering agent, water, a polyvinyl pyrrolidone and a butyl ester of polyvinylmethylether/maleic anhydride copolymer, wherein the pouch comprises an inner lining of linear low density polyethylene (LLDPE).

In another embodiment of this aspect, the present invention relates to an individually packaged wipe for the treatment of hyperhidrosis comprising glycopyrrolate at about 0.25 to about 6% w/w, wherein said wipe is contained within a pouch resistant to leakage, which further comprises ethanol, a buffering agent, water, a polyvinyl pyrrolidone and a butyl ester of polyvinylmethylether/maleic anhydride copolymer, wherein the buffering agent comprises citric acid and sodium citrate to maintain a pH of about 3.5 to about 6. In another embodiment, the buffering agent may comprise citric acid and tromethamine to maintain a pH of about 3.5 to about 6. The pH is preferably maintained at about 4±0.5, or about 4 to about 5, more preferably at about 4.5.

In another embodiment of this aspect, the present invention relates to an individually packaged wipe for the treatment of hyperhidrosis comprising glycopyrrolate at about 0.25 to about 6% w/w, wherein said wipe is contained within a pouch resistant to leakage, which further comprises ethanol, a buffering agent, water, a polyvinyl pyrrolidone and a butyl ester of polyvinylmethylether/maleic anhydride copolymer, wherein the ethanol and water is in the weight ratio of about 50:50 to about 60:40. In another embodiment, the ethanol is present in the amount of about 53.7 to about 57.3% w/w, the buffering agent is in the amount of about 0.2 to about 0.5% w/w, the polyvinyl pyrrolidone is in the amount of about 4% w/w, the butyl ester of polyvinylmethylether/maleic anhydride copolymer is in the amount of about 0.25% w/w and the water is added to 100% w/w.

Another aspect of the present invention relates to a method for alleviating hyperhidrosis in a mammal comprising the topical administration of an individually packaged wipe according to the various embodiments of the present invention, to an area of the body such that the hyperhidrosis is substantially reduced.

Still another aspect of the present invention relates to a method of preparing an individually packaged wipe for the treatment of hyperhidrosis comprising the steps of (a) contacting a wipe with a solution comprising glycopyrrolate at about 0.25 to about 6% w/w until wet; and (b) sealing the wipe of step (a) in a pouch resistant to leakage. In this aspect, the pouch preferably comprises an inner lining of linear low density polyethylene (LLDPE).

In one embodiment of this aspect, the solution may further comprise ethanol, a buffering agent, and water. The buffering agent may preferably comprise citric acid and sodium citrate to maintain a pH of about 3.5 to about 6. The buffering agent may alternatively preferably comprise citric acid and tromethamine to maintain a pH of about 3.5 to about 6. The pH is preferably maintained at about 4 to 5, or about 4 to about 5, more preferably at about 4.5. Further, the ethanol and water is preferably in the weight ratio of about 40:60 to about 60:40. The weight ratio of 60:40 is more preferred. In another embodiment of this aspect, the ethanol is present in the amount of about 53.7 to about 57.3% w/w and the buffering agent is in the amount of about 0.2 to about 0.5% w/w, with water being added to 100% w/w.

In another embodiment of this aspect, the solution further comprises a polyvinyl pyrrolidone and a butyl ester of polyvinylmethylether/maleic anhydride copolymer, in addition to the ethanol, buffering agent and water. Preferably, the pouch comprises an inner lining of linear low density polyethylene (LLDPE), and the buffering agent comprises citric acid and sodium citrate or citric acid and tromethamine to maintain a pH of about 3.5 to about 6. The pH is preferably maintained at about 4 to 5, or about 4 to about 5, more preferably at about 4.5. Further, the ethanol and water is preferably in the weight ratio of about 50:50 to about 60:40. The weight ratio of 60:40 is more preferred. The ethanol is present preferably at about 53.7 to about 57.3% w/w, the buffering agent is at about 0.2 to about 0.5% w/w, the polyvinyl pyrrolidone is at about 4% w/w, and the butyl ester of polyvinylmethylether/maleic anhydride copolymer is at about 0.25% w/w, with water being added to 100% w/w.

BRIEF DESCRIPTION OF THE FIGURES

FIG. 1A illustrates examples of the materials used to package the present glycopyrrolate formulations into pouches. The sample shown on the left hand side has a Linear Low Density Polyethylene (LLDPE) lining and the other two samples have a BAREX lining. FIG. 1B illustrates the package interactions with the formulations according to the present invention.

FIG. 2 illustrates the extent of coverage of wipes dosed with an amount of solution that is 60% of full capacity. In particular, FIG. 2A illustrates the extent of coverage on a representative wipe after 40 days of storage in a sealed pouch. FIG. 2B illustrates the extent of coverage on a representative wipe after pressure has been applied to a wipe contained within a pouch, examined immediately after pressure application.

FIG. 3A illustrates the dose delivered to palms from two different sized wipes of 6"×4" and 4"×4". FIG. 3B illustrates the dose delivered to palms from two different sized wipes, 6"×3.75" and 4"×3.75", each of which respectively has two different thickness of 53 g/m$^2$ and 69 g/m$^2$.

FIG. 11A illustrates average HDSS scores for ES formulations and FIG. 11B illustrates average HDSS scores for EPX formulations.

FIG. 12A illustrates gravimetric analysis for the ES formulations and FIG. 12B illustrates gravimetric analysis for the EPX formulations.

DETAILED DESCRIPTION OF THE INVENTION

Definitions

Figure 1:
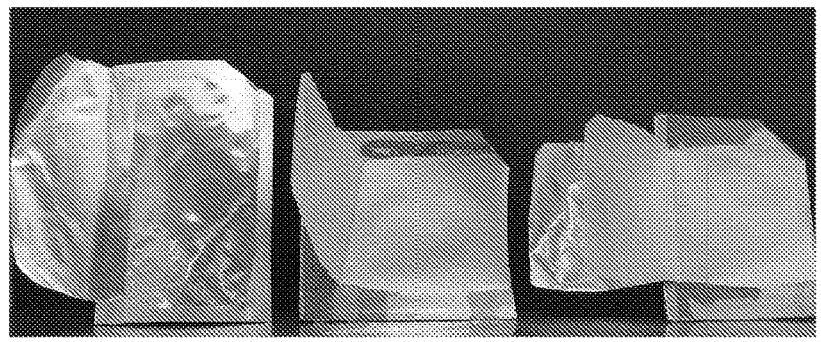
FIG. 1 illustrates the package materials used in the present invention. In particular.
Figure 1:
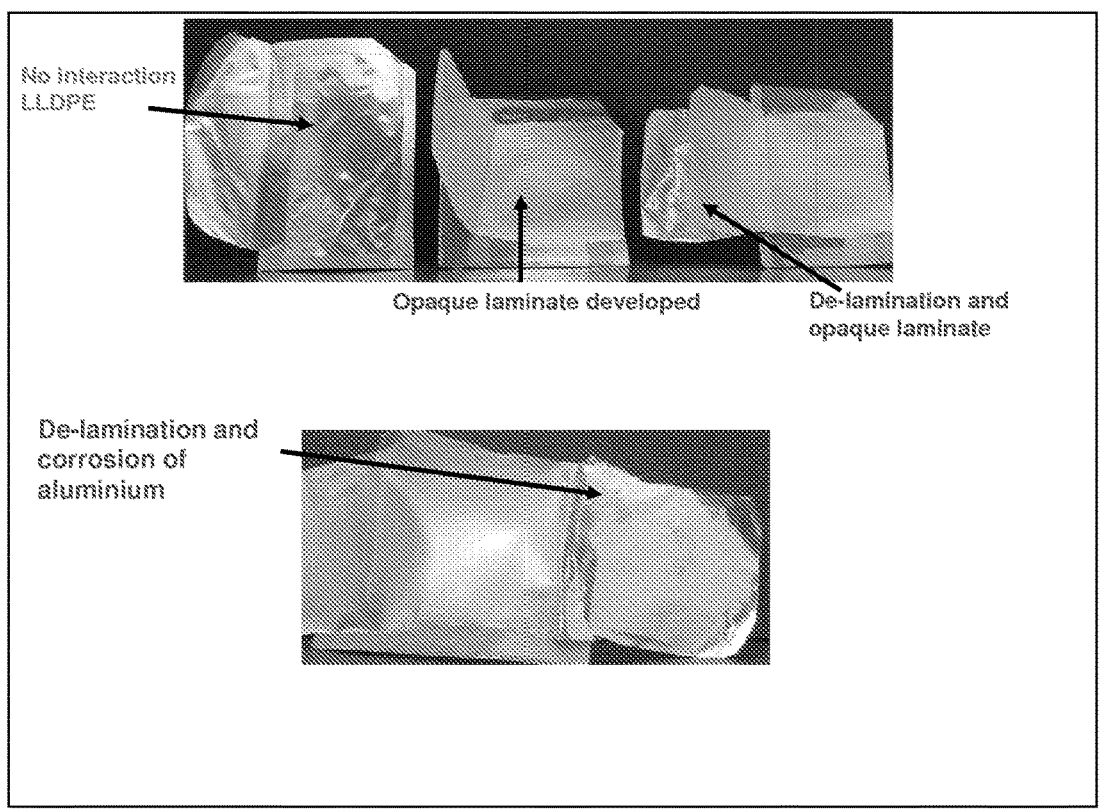

As used herein, the phrase "individually packaged" indicates that only one item is packaged in a particular package.

As used herein, the term "wipe" refers to a piece of material that can be topically applied. The wipe can be made of any suitable material, such as, for example, nonwoven material, paper material, woven material, knitted material, tufted material, stitch-bonded material incorporating binding yarns or filaments, or material felted by wet-milling.

As used herein, the term "pouch" refers to a structure that defines a discrete space into which a wipe/pad can be inserted.

As used herein, the phrases "simple solution" or "ethanolic solution" refer to alcohol/water based solutions which do not include a polymer system comprising a hydrophobic polymer in combination with a hydrophilic polymer. The phrases "ethanolic solution" or "ethanol solution" are particularly used herein to refer to ethanol/water based solutions, but it is not limited to refer only the ethanol/water based solutions. It may be used to refer to the simple solutions.

As used herein, the phrase "base solution" refers to the solutions comprising a glycopyrrolate compound as an active ingredient which is contacted with a wipe to prepare the individually packaged wipe formulations according to the present invention.

As used herein, the phrase "glycopyrrolate compound" means a compound of the formula:

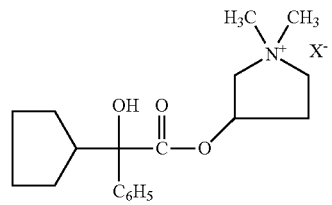

wherein X$^-$ is a pharmaceutically acceptable counter ion salt. The phrase "glycopyrrolate compound" as used herein also refers to analogues of glycopyrrolate capable of inhibiting hyperhidrosis wherein the chemical structure has been modified so as to introduce, modify and/or remove one or more functionalities of the structure. For example, such modification can result in the removal of an OH functionality, the introduction of an amine functionality, the introduction of a halo functionality, and the like. In so far as the glycopyrrolate analogues are capable of inhibiting hyperhidrosis they are encompassed by the definition of "glycopyrrolate compound".

As used herein, the phrase "pharmaceutically acceptable counter salt" refers to salts which retain the biological effectiveness and properties of the glycopyrrolate compound of the present invention, which are not biologically or otherwise undesirable, and which carry an anionic charge. The glycopyrrolate compounds of this invention form salts by virtue of the presence of the quaternary ammonium thereon.

As used herein, the term "treatment" refers to the process of producing an effect on biological activity, function, health, or condition of an organism in which such activity is maintained, enhanced, diminished, or applied in a manner consistent with the general health and well-being of the organism.

It is noted that, as used in the present application including this specification and the claims, the singular forms "a," "an" and "the" include plural references unless the context clearly dictates otherwise.

Further, it is noted that, as used in the present application including this specification and the claims, the range of values, such as concentration ranges, percentage ranges, or ratio ranges, is understood such that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the present invention, subject to any specifically excluded limit in the stated range. Where the stated range includes one or both of the limits, ranges excluding either or both of those included limits are also included in the present invention.

Further, for purposes of better understanding the present teachings and in no way limiting the scope of the teachings, unless otherwise indicated, all numbers expressing quantities, percentages or proportions, and other numerical values used in the specification and the claims, are to be understood as being modified in all instances by the term "about." Accordingly, unless indicated to the contrary, the numerical parameters set forth in the following specification and the claims are approximations that may vary depending upon the desired properties sought to be obtained. At the very least, each numerical parameter should at least be construed in light of the number of reported significant digits and by applying ordinary rounding techniques.

Unless defined otherwise, all other technical and scientific terms used herein have the same meaning as commonly understood to one of ordinary skill in the art to which the present invention pertains.

Preferred Embodiments

Glycopyrrolate Wipe Formulations

In a preferred embodiment of the present invention, the individually packaged wipe formulations comprising a glycopyrrolate compound include Ethanolic Solution (ES) wipe formulations and EPX™ wipe formulations. The glycopyrrolate ES formulations contain an alcohol/water based solution comprising glycopyrrolate, as an active ingredient, dehydrated alcohol (e.g., ethanol) and water, as a solvent system, and anhydrous citric acid and sodium citrate, as a buffering agent. The glycopyrrolate EPX™ wipe formulations also contain an ethanol/water based solution comprising glycopyrrolate, as an active ingredient, dehydrated alcohol (e.g., ethanol) and water, as a solvent system, anhydrous citric acid and sodium citrate, as a buffering agent, and polyvinyl pyrrolidone and butyl ester of polyvinylmethylether/maleic anhydride (PVM/MA) copolymer, as a polymer system comprising a hydrophobic polymer in combination with a hydrophilic polymer. The polymer system EPX™ is patented to Tomlinson (U.S. Pat. No. 6,211,250) and the context of U.S. Pat. No. 6,211,250 is incorporated herein by reference in its entirety. Quantitative composition of the ES and EPX wipe formulations are shown in Table 1.

TABLE 1

Quantitative composition of ES and EPX formulations.

| Ingredient | ES (% w/w) | EPX (% w/w) |
|---|---|---|
| Glycopyrrolate | 0.25-6 | 0.25-6 |
| Water | Up to 100 | Up to 100 |
| Alcohol | 53.71-57.31 | 53.71-57.31 |
| Anhydrous Citric Acid | 0.13-0.14 | 0.13-0.14 |
| Sodium Citrate | 0.09-0.11 | 0.09-0.11 |
| Polyvinyl pyrrolidone | | 0.25-6 |
| Butyl Ester of PVM/MA Copolymer | | |

To prepare base solutions for the ES formulations, anhydrous citric acid, sodium citrate (dehydrate) and glycopyrrolate are added to a suitable vessel. To this vessel, purified water is added and the mixture is stirred until all solids are dissolved. Dehydrated alcohol is then added to the vessel and the mixture is stirred. For the base solutions of the EPX formulations, anhydrous citric acid, sodium citrate (dehydrate), polyvinyl pyrrolidone and glycopyrrolate are added to a suitable vessel. To this vessel, purified water is added and the mixture is stirred until all solids are dissolved. Dehydrated alcohol is then added to the vessel and the mixture is stirred. To this mixture, butyl ester of PVM/MA copolymer is added and stirred well until it is fully dissolved.

A required quantity of the base solutions prepared according to the aforementioned process is filled into a pouch that has been pre-sealed on three sides and contains a folded wipe. The quantity can be measured by weight or volume. The top of the open pouch is sealed with a heat sealer.

Components

1. Active Ingredient

A glycopyrrolate compound is an active ingredient of the individually packaged wipe formulations according to the present invention. As defined herein, the glycopyrrolate compound has the following formula:

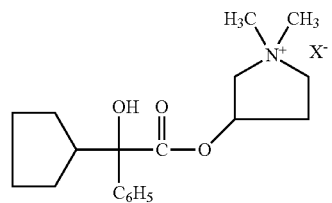

wherein the X⁻ is a pharmaceutically acceptable counter ion salt. The pharmaceutically acceptable counter salt may be prepared from inorganic and organic acids. Salts derived from inorganic acids include, but are not limited to, hydrochloric acid, hydrobromic acid, hydrogen fluoride, hydrogen iodide, sulfuric acid, nitric acid, phosphoric acid, and the like. Salts derived from organic acids include, but are not limited to, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Hydrobromic acid is preferred.

Glycopyrronium bromide, namely glycopyrrolate, has the chemical name of 3-[(cyclopentylhydroxyphenylacetyl)oxy]-1, 1-dimethylpyrrolidinium bromide. It is anticholinergic and less likely to cross lipid membranes (i.e., blood brain barrier), therefore fewer CNS effects are expected. Glycopyrrolate has a good tolerability with no significant systemic or local side effects. It does not occlude the follicular opening. Further, glycopyrrolate has significantly less cutaneous irritation as compared to the other aluminium chloride topical formulations for the treatment of hyperhydrosis.

The glycopyrrolate compound is effective over a wide dosage range and is generally administered in a therapeutically effective amount. Preferably the glycopyrrolate solutions, which are contacted with a wipe, contain from about 0.25 to about 6% w/w and more preferably from 0.5% to 4% w/w of glycopyrrolate. It will be understood, however, that the amount of the glycopyrrolate actually administered may be determined by a physician in light of the relevant circumstances, including the condition to be treated, the actual compound to be administered and its relative activity, the area to be administered, the response of the individual patient, the severity of the patient's symptoms, and the like.

Glycopyrrolate is readily commercially available. Glycopyrrolate can also be made as follows: α-phenylcyclopentaneglycolic acid is esterified by refluxing with methanol in the presence of hydrochloric acid and the resulting ester is transesterified with 1-methyl-3-pyrrolidinol using sodium as a catalyst. The transester is then reacted with methyl bromide to give glycopyrrolate. See U.S. Pat. No. 5,525,347 to Kellner et al. and U.S. Pat. No. 2,956,062 to Lunsford et al.

2. Solvent System

It is important that glycopyrrolate is soluble in the formulations when used, as the delivery to the skin is from a wipe. Particles of the active ingredient in the formulations would become trapped on the wipe resulting in dose variation.

A solvent system that is used for the present invention is an alcohol. Although skin safe alcohols such as ethanol, isopropanol, acetone, etc. may be used for the present formulations, an ethanol and water combination was found to be most preferable for the formulations. The combination of ethanol and water delivers the active ingredient to the skin in a cosmetically acceptable manner and ensures rapid drying of formulations, which is important for treating hyperhydrosis. The ethanol/water solvent system is also preferable in that it can solubilize the hydrophilic and hydrophobic polymer combinations in the EPX formulations. An ethanol content that is too high is undesirable due to the drying effect on the skin that this could cause.

Figure 5:
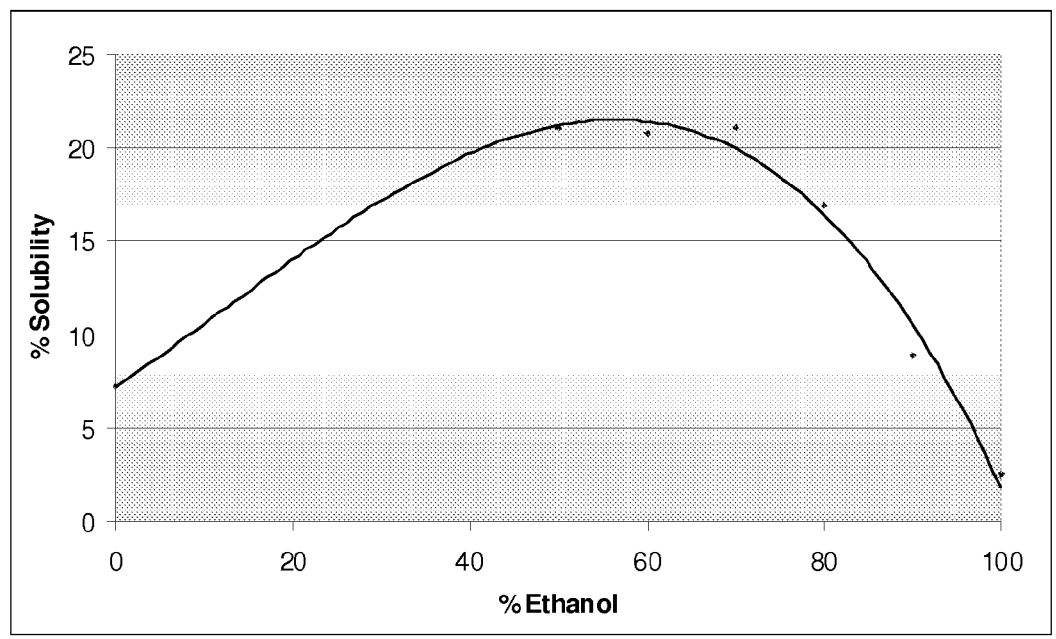
FIG. 5 illustrates the solubility of glycopyrrolate at 5° C.

The solubility of glycopyrrolate in various ethanol/water ratios at 5° C. was examined by HPLC assay. The results are shown in FIG. 5. FIG. 5 indicates that the maximum glycopyrrolate solubility in the ethanol/water solvent occurs over a ratio range from 50:50 to 70:30 and the maximum glycopyrrolate solubility was 21% w/w.

An ethanol/water ratio of 60:40 was identified as the most preferable ratio. At this ratio, the glycopyrrolate solubility is at a maximum, and is well in excess of the expected maximum drug level of 6%. 20% drug formulations were able to be made for pre-clinical toxicology studies. A minimum ethanol/water ratio of 50:50 was found to maintain the solubility of butyl ester of PVM/MA copolymer.

The 60:40 ratio in the final formulations is considered sufficient to allow leeway for the polymer solubility, but without excessive drying of the skin due to a higher ethanol level. The ratio of ethanol to water is a critical factor in maintaining the solubility of glycopyrrolate and the butyl ester of PVM/MA Copolymer in the formulations. Therefore, when the level of the active ingredient is modified, the levels of both ethanol and water are adjusted to maintain a 60:40 ratio. Base solutions for both EPX and ES formulations were made with 20% glycopyrrolate for pre-clinical toxicology studies without precipitation occurring in the formulation. Increasing the ethanol/water above 60:40 is not desirable as this would increase the risk of ethanol drying the skin.

3. Buffering Agent

Any buffering agent that has a good solubility in the solvent system of the formulations according to the present invention and can maintain a pH of about 3.5 to about 6, may be used for the present invention. Non-limiting examples of the buffering agent include any known buffering agent that can be compatible with a glycopyrrolate compound, such as, citric acid, sodium citrate, tromethamin, phosphate buffers, hydrochloride, etc. The buffering agent comprising citric acid and sodium citrate or citric acid and tromethamine is preferred, the combination of citric acid and sodium citrate being more preferred. 10 mM of total buffer was found to be a satisfactory level of buffer based on stability studies.

When used for the present formulations, the buffering agent is preferably in the amount of about 0.2 to about 0.5% w/w. Preferably, anhydrous citric acid is added in the amount of about 0.13 to 0.14% w/w and sodium citrate (dehydrate) is added in the amount of 0.09 to 0.11% w/w.

The buffering agent maintains the pH of the formulations at about 3.5 to about 6, preferably at about 4 to 5, most preferably at 4.5. The glycopyrrolate degradation rate is too high in the formulations with pH>6.0 with any of the buffer systems. Citric acid and sodium citrate were identified as preferable buffering agents to achieve and maintain the satisfactory pH range. The level of glycopyrrolate was found to change the pH of the formulations. Therefore, the ratio of buffer required to achieve the target pH requires modification for some glycopyrrolate levels.

Due to the potential for increased glycopyrrolate degradation identified in the initial stability studies, the total buffer level is reduced to 10 mM. This level was used in two stability studies of the final formulation and container closure. One study was at the target pH of 4.5, with drug levels of 2% and 4%. The study duration was 1 year at 25° C. and 30° C. and 6 months at 40° C. Both 2% and 4% formulations showed a similar and acceptable drug stability. pH drift was also the same for the two glycopyrrolate levels and found to be acceptable.

The second stability study examined 2% glycopyrrolate formulations at pH 4.0, 5.0 and 5.4 and both 10 mM and 20 mM total buffer. Little difference was found between the results of the 10 mM and 20 mM buffer levels. The stability of the glycopyrrolate was satisfactory at pH 4.0 and 5.0, but less satisfactory at pH 5.4. Therefore, the pH is more preferable at 4.5±0.5.

Figure 6:
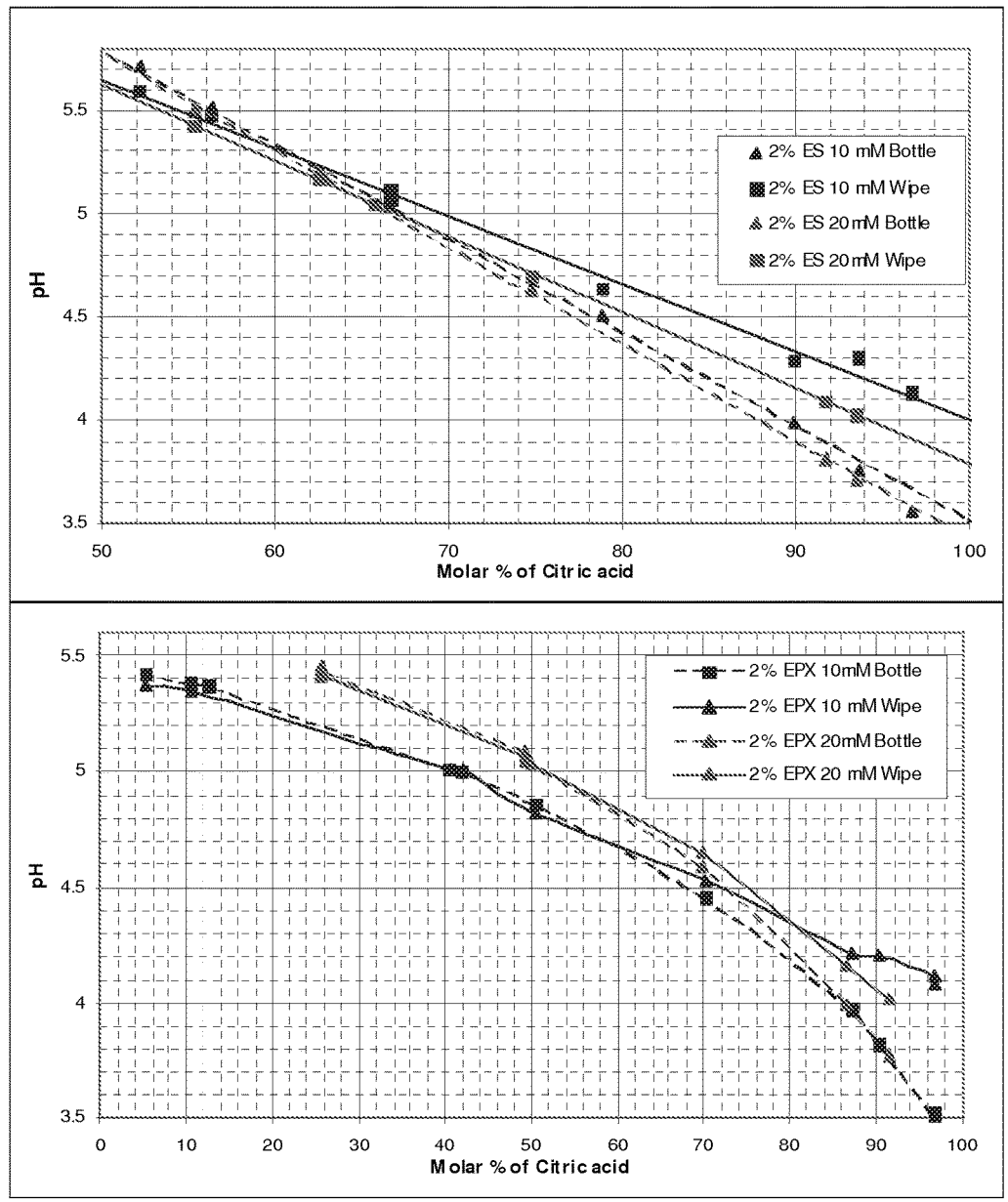
FIG. 6 illustrates a pH of base and wipe solutions versus buffer ratio for Ethanolic Solutions (ES) (top) and EPX™ (bottom) formulations.

Selecting the appropriate buffer ratio for a 2% glycopyrrolate formulation to achieve the desired pH was accomplished by plotting the buffer ratio versus pH for several formulations. See FIG. 6. Both the base solution and wipe solution (the solution obtained from a squeezed wipe) was measured. As the pH of the base solution decreased below pH 5, it was found that the wipe solution pH was higher than the base solution. The wipe solution pH was considered to be the pH of the formulations, as this is the material that is applied to the skin. Therefore, the buffer ratio was adjusted to achieve the desired pH for the wipe solution.

Glycopyrrolate was found to be slightly acidic and reduced the formulation pH. For the 4% glycopyrrolate formulation the difference in pH was less than 0.1, so the same buffer ratio as used for the 2% glycopyrrolate formulation was used. For the 6% EPX formulation and 20% EPX base solution (which is required for pre-clinical toxicology studies) the buffer ratio was slightly adjusted to achieve the most preferable pH of 4.5.

An investigation was conducted to determine the source of the change in pH between the base and wipe solutions. Measurement of the pH and conductivity of various solutions, including water and ethanol/water, indicated that a small amount of ionic material was extracted from the wipe and caused the pH of the wipe to be buffered towards pH 5.

4. Polymer System

The polymer system used in the present invention comprises a hydrophobic polymer (e.g., butyl ester of PVM/MA copolymer) in combination with a hydrophilic polymer (e.g., polyvinyl pyrrolidone, Povidone K-90). Non-limiting examples of the hydrophobic polymer include octylacrylamide octylpropenamide acrylate copolymer, aminoalkyl methacrylate copolymer, ammonio methacrylate copolymer, PVP/VA copolymer, PVA, butylester of PVM/MA copolymer, shellac and alkyl acrylates and copolymers thereof. Non-limiting examples of the hydrophilic polymer include hydroxypropylmethyl cellulose, hydroxypropyl cellulose, polyvinyl pyrrolidone (PVP), carbomer, PVM/MA decadiene cross polymer and hydroxypropylguar & copolymers thereof. Butyl ester of PVM/MA copolymer is most preferable for the hydrophobic polymer and polyvinyl pyrrolidone is most preferable for the hydrophilic polymer in the present formulations. Butyl ester of PVM/MA copolymer not only increases water resistance, but also does not have a high pH and thus is compatible with glycopyrrolate and is soluble in an ethanol/water solvent system, while insoluble in water only. Polyvinyl pyrrolidone not only has excellent rub-resistance, but also is not affected by pH and has a low susceptibility to ions. The hydrophobic polymer in combination with the hydrophilic polymer is a patented technology (EPX) to resist accidental removal of the active ingredient from the site of application/activity by enhancing rub and water resistance.

Figure 7:
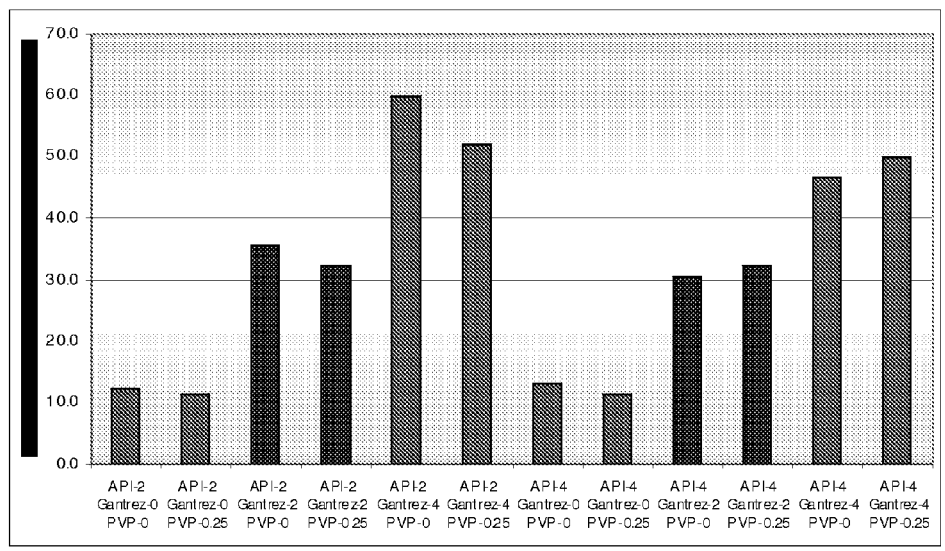
FIG. 7 illustrates the moist robustness results of the formulations having different level of butyl ester of polyvinylmethylether/maleic anhydride (PVM/MA) copolymer and polyvinyl pyrrolidone.

An increase of the level of butyl ester of PVM/MA copolymer increases the resistance of the glycopyrrolate to rubbing by a moist cloth, and increases its water resistance. A level of 4% is preferable for the present formulations. FIG. 7 shows the moist robustness results of the formulations having different levels of butyl ester of PVM/MA copolymer. Above this level the formulations are cosmetically unacceptable, and there is an increased risk of reducing the availability of glycopyrrolate for absorption into the skin.

Figure 8A:
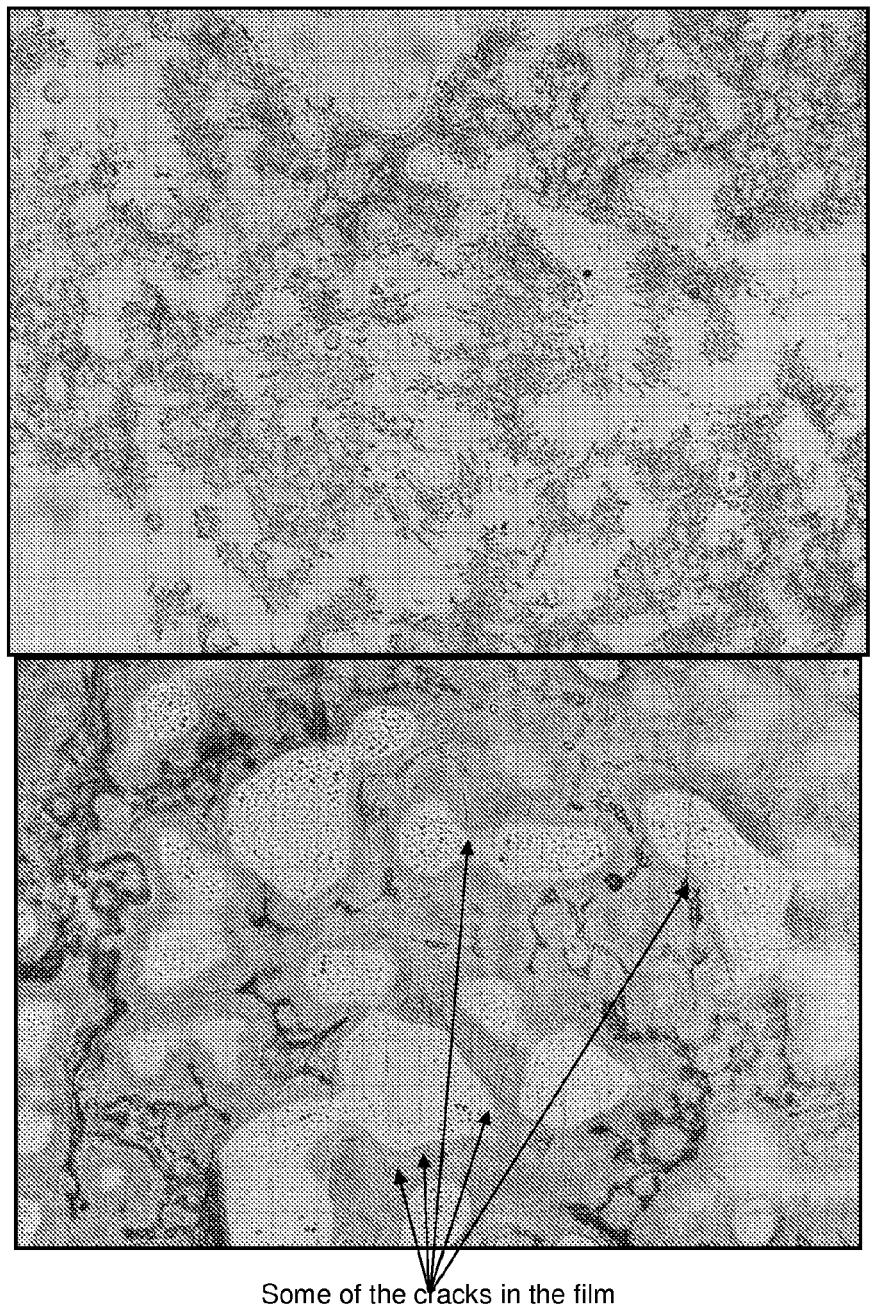
FIG. 8A illustrates photos of the dried EPX film obtained by the EPX formulations with and without povidone K90 bent to a 4.7 cm diameter.

Polyvinyl pyrrolidone, or Povidone K-90, increases the flexibility of the dried film, reducing the risk of the cracking and flaking. If the dried film is inflexible, normal movement of the skin may result in flaking of the film and loss of the glycopyrrolate from the application site. Dried EPX films were assessed by light microscopy. The EPX Formulations were cast onto flexible plastic sheets and dried at various temperatures and humidities. After drying, samples from the plastic sheet were bent around cylinders with various circumferences and each inspected for cracks by light microscopy. By comparing the number and size of cracks for the samples that had been bent to varying degrees, the relative flexibility of different formulations could be determined. FIG. 8A illustrates photos of the EPX formulation with and without povidone K90 bent to a 4.7 cm diameter. With povidone K90 there are no cracks visible, but without povidone K90 large vertical cracks are present in the film. Even when the formulation without povidone K90 was bent by a lesser amount (to 6.9 cm and 7.9 cm diameter) cracks in the film still occurred, but they were reduced in number and size as the diameter size became larger.

Figure 8B:
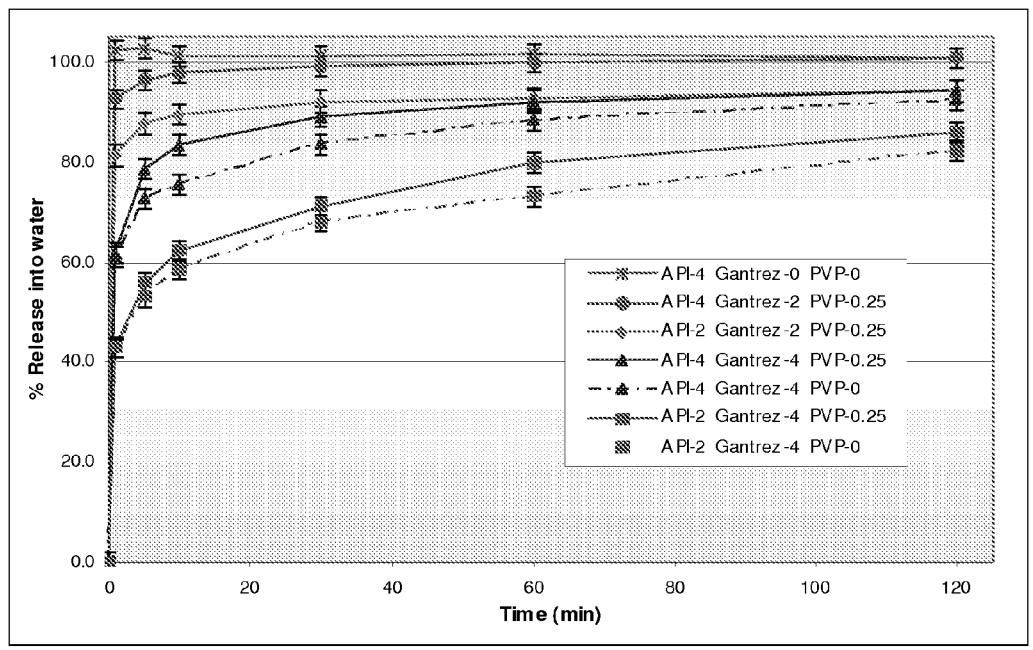
FIG. 8B illustrates water release from dried films of the base solution.
Figure 9:
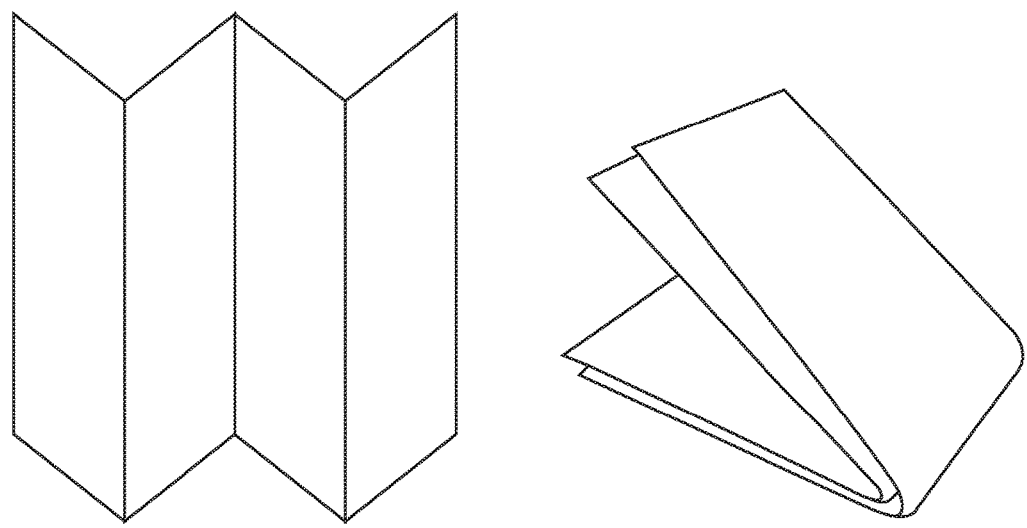
FIG. 9 illustrates a wipe fold and a pouch according to the present invention. The wipe would have a three-fold in one direction with a final center fold in the other direction as shown in FIG. 9.
Figure 9:
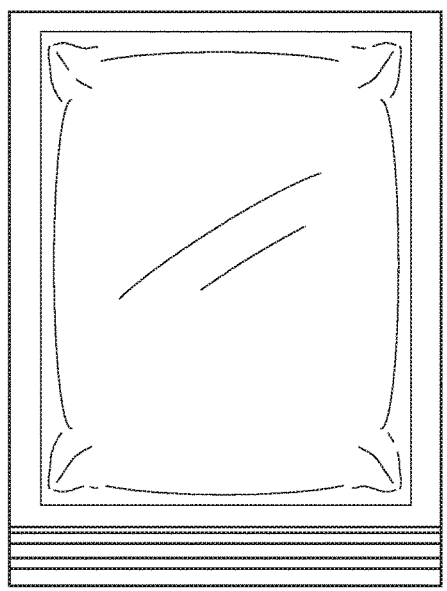

Water release studies indicate that the povidone K-90 improves the transport of glycopyrrolate from the dried film to be available for absorption into the skin. The preferable level for Povidone K-90 is 0.25%. FIG. 8B illustrates the results of the water release studies. The water release curve in FIG. 8B also indicates that povidone K-90 may assist in migration of glycopyrrolate from the film into the skin. Formulations with and without povidone K-90 had the same release at the initial time point, but then had a slightly faster release at subsequent time points.

5. Preservatives

In a preferred embodiment of the present invention, the glycopyrrolate formulations consist of a 60:40 ethanol/water solution and the wipes are packaged as sealed single use pouches. Accordingly, the present formulations are not expected to support microbial growth and no preservative is required. Tables 24 and 25 in Example 10 present a MLT (Microbial Limits Test) and an AET (Antimicrobial Effectiveness Test) performed on the glycopyrrolate EPX 2% and 4% formulations. All results are <10 or not detected for all organisms and time points.

6. Optional Additives

In an embodiment of the present invention, the present formulations may comprise one or more optional additives such as humectants, colorants, perfumes, etc. In practice, each of these optional additives should be both miscible and compatible with the glycopyrrolate compound. Compatible additives are those that do not prevent the use of the glycopyrrolate compound in the manner described herein. Non-limiting examples of the humectants include propylene glycol, sorbitol, glycerin, etc. Propylene glycol is preferred. When included, propylene glycol may be used in the amount of 2% w/w to 4% w/w.

7. Wipe

For a wipe, Tudor 6" AP686 69 g/m$^2$ is preferably used. The size of the wipe in flat form is preferably about 4"-6"×3.78"-4". In particular, about 6"×4", about 6"×3.78", about 5"×4", about 5"×3.78", about 4"×4", or about 4"×3.78" can be preferably used. As folded, 1.5"×2"±0.125" or 1.5"×1.875"±0.125" is preferably used. The wipe has three folds along the long side, then in half across the other orientation during insertion into a laminated pouch as shown in FIG. 2C, which has been pre-sealed on three sides.

8. Pouch

The pouch used in the present invention is resistant to leakage. Preferably, it comprises an inner lining of linear low density polyethylene (LLDPE). The laminate has the composition, Glenroy: 0.48 mil PET/0.75 mil LDPE/0.285 mil Foil/0.75 mil CRC-1/1.50 mil LLPDEF. The pouch size is not limited, but 2.375"×3.5"±0.0625" is preferred.

EXAMPLES

The following examples illustrates the present topical formulations, but they are not intended to limit the present claims.

Example 1

Preparation of Glycopyrrolate Formulations

A: Glycopyrrolate Ethanolic Solutions (ES) Formulations

Glycopyrrolate ES formulations were prepared by adding the buffering agents, anhydrous citric acid (USP) and dehydrate sodium citrate (USP) to a beaker in the amounts in Table 2, and then, adding purified water thereto and stirring until they are dissolved. To this mixture, dehydrated alcohol in the amount of Table 2 was added and stirred to mix. 0 to 20% w/w of glycopyrrolate was then added and stirred until it was dissolved in the mixture. A placebo formulation was prepared for the clinical trials and 20% glycopyrrolate formulation was prepared for the toxicological test.

TABLE 2

Composition of Glycopyrrolate ES formulations (All levels listed are % w/w.)

| | | | API Level | | | |
|---|---|---|---|---|---|---|
| | | Placebo | 2% | 4% | 6% | 20% |
| | | | Formulation No | | | |
| | Grade | 640/1/3 | 640/1/1 | 640/1/2 | 710/1/11 | 710/1/9 |
| Glycopyrrolate | USP | 0.00 | 2.00 | 4.00 | 6.00 | 20.00 |
| Purified Water | USP | 39.92 | 39.12 | 38.32 | 37.52 | 31.91 |

TABLE 2-continued

Composition of Glycopyrrolate ES formulations (All levels listed are % w/w.)

| | | API Level | | | | |
|---|---|---|---|---|---|---|
| | | Placebo | 2% | 4% | 6% | 20% |
| | | | | Formulation No | | |
| | Grade | 640/1/3 | 640/1/1 | 640/1/2 | 710/1/11 | 710/1/9 |
| Dehydrated alcohol | USP | 59.87 | 58.67 | 57.47 | 56.27 | 47.86 |
| Anhydrous Citric Acid | USP | 0.15 | 0.15 | 0.15 | 0.15 | 0.15 |
| Sodium Citrate (Dihydrate) | USP | 0.06 | 0.06 | 0.06 | 0.06 | 0.08 |

B: Glycopyrrolate EPX Formulations

Glycopyrrolate EPX formulations were prepared by adding the buffering agents, anhydrous citric acid (USP) and sodium citrate (dihydrate) (USP) to a beaker in the amounts in Table 3, followed by adding purified water thereto and stirring it until dissolved. To this mixture, dehydrated alcohol in the amount of Table 3 was added and stirred to mix. 0.25% w/w of povidone K90 and 4% w/w of Butyl Ester of PVM/MA Copolymer were added and stirred until fully dissolved. Lastly, 0 to 20% w/w of glycopyrrolate was added to the mixture and stirred until fully dissolved. A placebo formulation was prepared for the clinical trials and 20% glycopyrrolate formulation was prepared for the toxicological test.

TABLE 3

Composition of Glycopyrrolate EPX Formulations (All levels listed are % w/w.)

| | | API Level | | | | |
|---|---|---|---|---|---|---|
| | | Placebo | 2% | 4% | 6% | 20% |
| | | | | Formulation Number | | |
| | Grade | F640/1/6 | F640/1/4 | F640/1/5 | F710/1/12 | F710/1/10 |
| Glycopyrrolate | USP | 0.00 | 2.00 | 4.00 | 6.00 | 20.00 |
| Purified Water | USP | 38.21 | 37.41 | 36.61 | 35.80 | 30.20 |
| Dehydrated Alcohol | USP | 57.31 | 56.11 | 54.91 | 53.71 | 45.31 |
| Anhydrous Citric Acid | USP | 0.14 | 0.14 | 0.14 | 0.13 | 0.12 |
| Sodium Citrate (Dihydrate) | USP | 0.09 | 0.09 | 0.09 | 0.11 | 0.12 |
| Povidone K90 | USP | 0.25 | 0.25 | 0.25 | 0.25 | 0.25 |
| Butyl Ester of PVM/MA Copolymer[1] (Gantrez ES-425) | IIG | 4.00 | 4.00 | 4.00 | 4.00 | 4.00 |

Note:
[1]Expressed as the level of Butyl Ester of PVM/MA Copolymer. As this is supplied as a 50% solution in ethanol, the level of Gantrez ES-425 in a formulation batch sheet will be 2 times the level shown above (i.e. 8.0%). The batch sheet must also account for the ethanol content in the Gantrez ES-425 and 4.0 must be deducted from the dehydrated alcohol to be added to the formulation.

Example 2

Determination of Glycopyrrolate Stability

In order to assess the stability of glycopyrrolate in solution form and in EPX™ gel form under various buffer and storage conditions, formulations of glycopyrrolate were stored in glass bottles or in pouches under the conditions indicated below. The rate modulating EPX gel technology is described in U.S. Pat. No. 6,211,250, the entire contents of which are incorporated herein by reference. As set out in Table 5, polyvinyl pyrrolidone and a butyl ester of polyvinylmethylether/maleic anhydride copolymer are used as polymers to modulate the rate of release of the glycopyrrolate (in accordance with the EPX rate modulating polymeric technology described in U.S. Pat. No. 6,211,250).

To examine the effect of different buffers at different ranges of pH, the buffer systems shown in Table 1 were tested.

TABLE 4

| pH Range | Citric/Citrate | Citric Tromethamine | Phosphate |
|---|---|---|---|
| Ethanol solution | 4.1-7.4 | 4.0-6.0 | 3.3-7.1 |
| EPX | 3.9-5.4 | 4.1-5.5 | 3.0-6.5 |

Table 5 shows the formulations of the ethanol solution and EPX gel tested.

TABLE 5

| Ingredient | Ethanol solution | EPX |
|---|---|---|
| Glycopyrrolate | 2.00 | 2.00 |
| Water | 38.27 | 36.50 |
| Ethanol | 57.40 | 54.75 |
| Propylene glycol | 2.00 | 2.00 |
| Buffer | 0.2-0.5 | 0.2-0.5 |
| PVP K-90 | — | 0.50 |
| Gantrez ES 425 | — | 4.00 |

In one set of experiments, both formulations of glycopyrrolate were stored in glass bottles at 5° C., 25° C., and 40° C. Analytical analyses of glycopyrrolate degradation and pH measurements were made at 1 and 2 month time points.

In another set of experiments, 2 ml of each formulation was added to pouches (without the wipe material). Five pouch materials were assessed: SURLYN, EAA, 2 mil Barex, 3.5 mil Barex and LLDPE. 2 to 3 pouches were made for each formulation and each pouch material. The pouches were stored at 50° C. Weight loss was measured at 1 and 2 months. At different time points, selected pouches were opened and assessed for packaging interactions. At 2 months, selected pouches were also analyzed by HPLC to monitor degradation of glycopyrrolate, and a measurement of pH was taken.

The results of the analytical analyses on the stability of various glycopyrrolate formulations packaged with different pouch materials is shown in Tables 3 to 6 below. Potency results were found to have a good correlation with the % area of glycopyrrolate degradants. Selected formulations were also analyzed after 2 months at 25° C.

TABLE 6

Ethanol solution formulations of glycopyrrolate stored in glass bottles - Analytical Analysis (% Area of Glycopyrrolate Degradants)

| F# | Buffer Components | Buffer % w/w | Initial** pH | 1 mth 40° C. | 2 mth 40° C. |
|---|---|---|---|---|---|
| 585/29/15 | Phosphoric acid and Sodium phosphate monobasic | 0.14:0.12 | 3.28 | 0.5 | 0.8 |
| 585/29/16 | Phosphoric acid (adjusted with sodium hydroxide) | 0.28:+0.15 | 4.47 | 1.0 | 1.1 |
| 585/29/4 | Citric Acid and Sodium Citrate | 0.32:0.084 | 4.07 | 0.3 | 0.2 |
| 585/29/6 | Citric Acid and Sodium Citrate | 0.19:0.29 | 5.70 | 1.8 | 2.9 |
| 585/29/13 | Citric Acid and Sodium Citrate (buffer precipitated) | 0.054:0.51 | 7.13 | 19.1 | |
| 585/29/18 | Citric Acid and Sodium Citrate (Reduced buffer = 10 mM) | 0.024:0.26 | 7.39 | 18.0 | 22.4 |
| 585/29/19 | Citric Acid and Sodium Citrate (EtOH/Water = 40/60) | 0.19:0.29 | 5.24 | 1.0 | 1.8 |
| 585/29/20 | Citric Acid and Sodium Citrate same ratio as F585/29/6 (EtOH/Water = 40/60) | 0.14:0.37 | 5.82 | 3.0 | 4.9 |
| 585/31/3 | Citric Acid and Tromethamine | 0.40:0.10 | 4.02 | 0.1 | 0.2 |
| 585/31/4 | Citric Acid and Tromethamine | 0.25:0.25 | 5.99 | 2.3 | 3.8 |
| 585/29/17 | Sodium phosphate monobasic and sodium phosphate dibasic | 0.14:0.0036 | 7.09 | 3.9 | |

**Initial pH taken from 1 month 5° C. data

TABLE 7

Ethanol solution formulations of glycopyrrolate packaged in pouches after 2 months at 50° C. - Analytical Analysis

| F# | Buffer Components | pH | EAA | SURLYN | 2 mil BAREX | LLDPE |
|---|---|---|---|---|---|---|
| 585/29/4 | Citric Acid and Sodium Citrate | 4.07 | 0.8 | 0.8 | 0.4 | 0.4 |
| 595/6/1 | | 4.02 | | | | |
| 585/29/6 | Citric Acid and Sodium Citrate | 5.70 | 8.9 | 8.8 | 8.8 | 8.7 |
| 595/6/2 | | 5.65 | | | | |
| 585/29/19 | Citric Acid and Sodium Citrate (EtOH/Water = 40/60) | 5.24 | 6.0 | 7.4 | 6.2 | 6.0 |
| 595/6/5 | | 5.26 | | | | |
| 595/6/6 | Citric Acid and Sodium Citrate (EtOH/Water = 40/60) | 5.67 | | | 11.3 | 11.2 |

TABLE 8

EPX formulations of glycopyrrolate stored in glass bottles - Analytical Analysis (% Area of Glycopyrrolate Degradants)

| F# | Buffer Components | Buffer % w/w | Initial pH | 1 mth 40° C. | 2 mth 40° C. |
|---|---|---|---|---|---|
| 595/3/1 | Citric Acid and Sodium Citrate | 0.33:0.085 | 3.90 | 0.3 | 0.4 |
| 595/3/2 | Citric Acid and Sodium Citrate | 0.19:0.29 | 5.03 | 0.5 | 0.9 |
| 595/3/3 | Citric Acid and Sodium Citrate (Reduced buffer = 10 mM) | 0.024:0.26 | 5.37 | 0.6 | 1.1 |
| 595/3/10 | Citric Acid and Tromethamine | 0.37:0.13 | 4.11 | 0.3 | 0.5 |
| 595/3/11 | Citric Acid and Tromethamine | 0.13:0.37 | 5.51 | 0.8 | 1.4 |
| 595/3/8 | Phosphoric acid (adjusted with sodium hydroxide) | 0.23:+0.18 | 2.97 | 0.3 | 0.2 |
| 595/3/6 | Sodium phosphate monobasic and sodium phosphate dibasic | 0.18:0.0047 | 4.42 | 0.4 | 0.8 |
| 595/3/13 | Sodium phosphate monobasic (adjusted with sodium hydroxide) | 0.18:+ | 5.48 | 1.0 | 1.7 |
| 595/3/14 | Sodium phosphate monobasic (adjusted with sodium hydroxide) | 0.18:+ | 6.48 | 3.5 | 4.6 |
| 595/3/15 | Sodium phosphate monobasic (adjusted with sodium hydroxide) 0.25% PVP | 0.18:+ | 6.48 | 3.5 | 4.6 |

TABLE 9

EPX formulations of glycopyrrolate packaged in pouches after 2 months at 50° C. - Analytical Analysis

| F# | Buffer Components | pH | EAA | SURLYN | 2 mil BAREX | LLDPE |
|---|---|---|---|---|---|---|
| 595/3/1 | Citric Acid and Sodium Citrate | 3.90 | 1.1 | 1.2 | 1.0 | 1.0 |
| 595/3/2 | Citric Acid and Sodium Citrate | 5.03 | 2.5 | 2.8 | 2.4 | 2.4 |

The data in Tables 6 to 9 indicate that glycopyrrolate in the various formulations and in the various pouch materials tested was more stable at lower pH. Above pH 6.0, the degradation rate accelerates, and is unlikely to afford a shelf-life of 2 years at 25° C. However, the results suggest that for both the ethanol solution and EPX formulations, the citric acid/sodium citrate buffer system at pH 4.0-5.0 provides good glycopyrrolate stability. No differences were observed between the five pouch linings with respect to degradation of glycopyrrolate upon storage. Furthermore, the degradation rate of glycopyrrolate after 2 months at 50° C. in pouches was consistent with the results for solutions stored in glass bottles after 2 months at 40° C.

Example 3

Determination of Glycopyrrolate Stability

To asses the stability of glycopyrrolate in final packaging, six ES and EPX formulations and two EPX placebo formulations comprising 2% glycopyrrolate, at pH 4.0, 5.0 or without buffer, were prepared principally according to the method described in Example 1. Composition of the formulations prepared is shown in Table 10. The buffer system was citric/citrate. The formulations were packaged as folded wipes stored in individual laminated foil pouches. Approximately 3.0 g of each formulation was added to each folded wipe and sealed in individual pouches. The test duration was for 3 months at 5° C., 25° C. and 40° C.

The used wipe and pouch was as follows:

Wipe: Tudor 6" AP686 69 g/m², three fold and final center fold.

Size: 6"×4"±⅛" (flat)

Loading: 55% of capacity—3.00 g—(3.35 mL)

Pouch: Glenroy 0.48 mil PET/0.75 mil LDPE/0.285 mil Foil/0.75 mil CRC-1/1.50 mil LLPDEF Size: 2.375"×3.5"+0.0625"

TABLE 10

Formulation Composition. All levels listed are % w/w.

| | 612/9/1 | 612/9/2 | 612/9/3 | 612/9/4 | 612/9/5 | 612/9/6 | 612/9/8 |
|---|---|---|---|---|---|---|---|
| Type | ES | ES | ES | EPX | EPX | EPX | Type |
| Target pH | 4.0 | 5.0 | None | 4.0 | 5.0 | None | Buffer |
| Glycopyrrolate | 2.00 | 2.00 | 2.00 | 2.00 | 2.00 | 2.00 | — |
| Water | 37.52 | 37.51 | 37.60 | 35.82 | 35.80 | 35.90 | 36.62 |
| Ethanol | 60.28 | 60.26 | 60.40 | 53.72 | 53.70 | 53.85 | 54.92 |
| Propylene glycol | 4.00 | 4.00 | 4.00 | 4.00 | 4.00 | 4.00 | 4.00 |
| Citric acid (anhydrous) | 0.17 | 0.13 | — | 0.17 | 0.10 | — | 0.17 |
| Sodium citrate dihydrate | 0.03 | 0.10 | — | 0.04 | 0.15 | — | 0.04 |
| Butyl Ester of PVM/MA Copolymer (Gantrez ES-425) | — | — | — | 4.00 | 4.00 | 4.00 | 2.00 |
| PVP | — | — | — | 0.25 | 0.25 | 0.25 | 0.25 |

To determine glycopyrrolate content of the pouches, first, wipe solutions were collected by transferring the folded wipe from an opened pouch into a large syringe, then pressing the syringe and collecting the solutions (wipe solution method). These solutions were then assayed for glycopyrrolate percentage by weight. Next, the entire wipe and the pouch was extracted and assayed for glycopyrrolate (total pouch extraction method). The result was then compared against the known weight of base solution added to each pouch.

The results are shown in Table 11. At T=0 and all 40° C. time points both assays were used and there did not appear to be any differences between the two methods. These results confirm that the API is not retained on the wipe, either initially or during storage. The only formulation to show a very high loss of glycopyrrolate was the ES without buffer. Both the ES and EPX at low pH were very stable, and the high pH had up to 1% glycopyrrolate loss after 3 months at 40° C. (as measured by degradants present). The EPX formulation without buffer was also very stable.

The pH drift in both type formulations were acceptable. In ES formulations, both pH 4.0 and 5.0 increased about 0.2 and was slowing. In EPX formulations, pH 4.0 decreased about 0.2 and pH 5.0 decreased about 0.4 and was slowing.

TABLE 11

Glycopyrrolate assay results. First number is the percentage of the T = 0 results and in brackets is the percentage of degradants.

|  |  | 612/9/1 | 612/9/2 | 612/9/3 | 612/9/4 | 612/9/5 | 612/9/6 |
|---|---|---|---|---|---|---|---|
|  |  | \multicolumn{6}{c}{Wipe Solution} |
|  | Type | ES | ES | ES | EPX | EPX | EPX |
|  | Buffer | 4.0 | 5.0 | None | 4.0 | 5.0 | None |
| Temp | T = 0 w/w | 2.021 | 2.008 | 1.971 | 2.021 | 2.017 | 2.002 |
| 5° C. | 1 mth | — | — | 100.0% (0.1) | — | — | — |
|  | 2 mth | — | — | 100.2% (0.1) | — | — | — |
|  | 3 mth | 99.4% (0.1) | — | — | — | — | — |
| 25° C. | 3 mth | — | 100.4% (0.1) | 100.0% (0.1) | — | 99.7% (0.2) | — |
| 40° C. | 1 mth | 98.3% (0.0) | 99.9% (0.2) | 94.7% (3.5) | 99.1% (0.1) | 100.6% (0.3) | 100.2% (0.2) |
|  | 2 mth | 99.7% (0.1) | 100.3% (0.4) | 94.3% (4.9) | 99.3% (0.3) | 98.1% (0.5) | 99.4% (0.3) |
|  | 3 mth | 99.6% (0.2) | 99.5% (0.8) | 93.5% (6.1) | 99.9% (0.5) | 99.9% (0.8) | 99.5% (0.5) |
|  |  | \multicolumn{6}{c}{Total Pouch Extraction} |
|  | Type | ES | ES | ES | EPX | EPX | EPX |
|  | Buffer | 4.0 | 5.0 | None | 4.0 | 5.0 | None |
| Temp | T = 0 w/w | 2.014 | 2.017 | 2.011 | 2.018 | 2.020 | 2.006 |
| 5° C. | 1 mth | — | — | — | 99.5% (0.0) | — | — |
|  | 2 mth | — | — | — | 100.6% (0.0) | — | — |
|  | 3 mth | — | — | — | 99.5% (0.1) | — | — |
| 25° C. | 3 mth | — | — | 98.1% (2.2) | 99.6% (0.3) | — | — |
| 40° C. | 1 mth | 99.3% (0.0) | 99.7% (0.2) | 96.4% (3.5) | 99.2% (0.1) | 98.8% (0.3) | 99.8% (0.2) |
|  | 2 mth | 98.4% (0.1) | 99.3% (0.4) | 95.3% (4.8) | 99.3% (0.3) | 98.7% (0.5) | 99.3% (0.3) |
|  | 3 mth | 99.7% (0.1) | 98.9% (0.8) | 94.2% (5.9) | 98.8% (0.5) | 98.4% (0.9) | 99.9% (0.5) |

Example 4

Determination of Glycopyrrolate Stability

This example establishes the chemical and physical stability of the formulations prepared according to Example 1A and 1B. The study duration was for 12 months at 25° C., 9 months at 30° C. and 6 months at 40° C. Six formulations, four containing glycopyrrolate and two placebos, were prepared according to Example 1A and 1B. The four glycopyrrolate formulations consist of two formulation variations, ES and EPX, each containing 2% and 4% glycopyrrolate. All formulations had a pH of about 4.5. The glycopyrrolate formulations were packaged as folded wipes stored in individual laminated foil pouches. Approximately 3.0 g of each formulation was added to each folded wipe and sealed in individual pouches.

The used wipe and pouch was as follows:
Wipe: Tudor 6" AP686 69 g/m$^2$
Size: 6"×3.75"±⅛" (flat)
Loading: 55% of capacity—3.00 g—(3.35 mL)
Pouch: Glenroy 0.48 mil PET/0.75 mil LDPE/0.285 mil Foil/0.75 mil CRC-1/1.50 mil LLPDEF
Size: 2.375"×3.5"±0.0625"

The results are shown in Table 10 as the glycopyrrolate percentage found in the wipe solution collected by squeezing the individual wipes, and in Table 13 as a percentage of the T=0 results. Table 14 shows the levels of the main Degradant peak D1. As shown in Tables 10-12, the loss of an active ingredient, glycopyrrolate, was low for both ES and EPX formulations, supporting a shelf-life of over 2 years at 25° C. However, for EPX formulations, degradant D1 was estimated to be approximately 1% of total peak area at 2 years at 25° C. At T=0 the assay of the distribution of glycopyrrolate across the wipe was reasonably even. All wipes examined visually at various time points appear to have an even formulation distribution. Weight loss was minimal.

TABLE 12

Results of glycopyrrolate assay, % w/w. Four pouches assayed at T = 0 and two pouches assayed at each subsequent time point. % of degradants calculated by percent normalisation of total peak area.

| Temp | Time point (months) | 640/6/1 % w/w | % of degradants | 640/6/2 % w/w | % of degradants | 640/6/4 % w/w | % of degradants | 640/6/5 % w/w | % of degradants |
|---|---|---|---|---|---|---|---|---|---|
|  | T = 0 | 2.027 | — | 4.07 | — | 2.015 | — | 4.06 | — |
| 5° C. | 1 | 2.018 | <0.1 | — | — | 2.031 | <0.1 | — | — |
|  | 2 | — | — | 4.06 | <0.1 | — | — | 4.08 | <0.1 |
|  | 3 | 2.026 | <0.1 | — | — | 2.024 | 0.1 | — | — |
|  | 6 | — | — | 4.07 | <0.1 | — | — | 4.09 | 0.1 |
|  | 9 | 2.016 | <0.1 | — | — | 2.029 | 0.1 | — | — |
|  | 12 | — | — | 4.01 | <0.1 | — | — | 4.01 | 0.1 |
| 25° C. | 3 | 2.036 | 0.1 | 4.11 | <0.1 | 2.053 | 0.2 | 3.96 | 0.2 |
|  | 6 | 2.014 | 0.1 | 4.06 | 0.1 | 2.035 | 0.3 | 4.04 | 0.1 |
|  | 9 | 2.005 | 0.2 | 4.05 | 0.2 | 2.007 | 0.5 | 4.03 | 0.4 |
|  | 12 | 2.005 | 0.2 | 4.10 | 0.2 | 2.036 | 0.6 | 4.03 | 0.5 |

TABLE 12-continued

Results of glycopyrrolate assay, % w/w. Four pouches assayed at T = 0 and two pouches assayed at each subsequent time point. % of degradants calculated by percent normalisation of total peak area.

| Temp | Time point (months) | 640/6/1 % w/w | % of degradants | 640/6/2 % w/w | % of degradants | 640/6/4 % w/w | % of degradants | 640/6/5 % w/w | % of degradants |
|---|---|---|---|---|---|---|---|---|---|
| 30° C. | 2 | 2.021 | 0.1 | 4.05 | 0.1 | 2.025 | 0.2 | 4.05 | 0.2 |
| | 3 | 2.046 | 0.1 | 4.08 | 0.1 | 2.018 | 0.3 | 4.07 | 0.3 |
| | 6 | 2.013 | 0.2 | 4.05 | 0.2 | 2.007 | 0.6 | 4.03 | 0.3 |
| | 9 | 2.017 | 0.3 | 4.05 | 0.3 | 2.010 | 0.8 | 4.06 | 0.7 |
| | 12 | 2.026 | 0.4 | 4.02 | 0.4 | 1.984 | 1.0 | 4.00 | 0.9 |
| 40° C. | 1 | 2.047 | 0.1 | 4.13 | 0.1 | 2.030 | 0.3 | 4.08 | 0.3 |
| | 2 | 2.026 | 0.2 | 4.10 | 0.2 | 1.948 | 0.5 | 4.10 | 0.4 |
| | 3 | 2.023 | 0.4 | 4.06 | 0.3 | 2.005 | 0.6 | 4.14 | 0.5 |
| | 6 | 1.996 | 0.6 | 4.06 | 0.5 | 1.984 | 1.3 | 3.98 | 0.4 |

TABLE 13

Results of glycopyrrolate assay, percentage of T = 0 results

| Temp | Time point (months) | 640/6/1 % w/w | 640/6/2 % w/w | 640/6/4 % w/w | 640/6/5 % w/w |
|---|---|---|---|---|---|
| | T = 0 w/w | 2.027 | 4.07 | 2.015 | 4.06 |
| 5° C. | 1 | 99.6 | — | 100.8 | — |
| | 2 | — | 99.8 | — | 100.5 |
| | 3 | 100.0 | — | 100.4 | — |
| | 6 | — | 100.0 | — | 100.7 |
| | 9 | 99.5 | — | 100.7 | — |
| | 12 | — | 99.3 | — | 99.3 |
| 25° C. | 3 | 100.4 | 101.0 | 101.9 | 97.5 |
| | 6 | 99.4 | 99.8 | 101.0 | 99.5 |
| | 9 | 98.9 | 99.5 | 99.6 | 99.3 |
| | 12 | 99.4 | 101.5 | 101.3 | 99.8 |
| 30° C. | 2 | 99.7 | 99.5 | 100.5 | 99.8 |
| | 3 | 100.9 | 100.2 | 100.1 | 100.2 |
| | 6 | 99.3 | 99.5 | 99.6 | 99.3 |
| | 9 | 99.5 | 99.5 | 99.8 | 100.0 |
| | 12 | 100.4 | 99.5 | 98.7 | 99.0 |
| 40° C. | 1 | 101.0 | 101.5 | 100.7 | 100.5 |
| | 2 | 100.0 | 100.7 | 96.7 | 101.0 |
| | 3 | 99.8 | 99.8 | 99.5 | 102.0 |
| | 6 | 98.5 | 99.8 | 98.5 | 98.0 |

TABLE 14

Degradant D1 levels at the 12 month time point (% of total area)

| 12 months | 640/6/1 | 640/6/2 | 640/6/4 | 640/6/5 |
|---|---|---|---|---|
| 5° C. | — | <0.1 | — | <0.1 |
| 25° C. | 0.15 | 0.14 | 0.52 | 0.46 |
| 30° C. | 0.34 | 0.27 | 0.92 | 0.84 |

Example 5 pH Effects on Glycopyrrolate Pouch/Wipe Formulations

This example demonstrates the pH effects on the glycopyrrolate pouch/wipe formulations. Six ES and seven EPX glycopyrrolate formulations were made according to the process described in Example 1. Two buffer levels were used and the buffer ratios were adjusted to achieve a final pH as close as possible to 4.0, 5.0 and 5.4 (as measured in the wipe solution) for each of the formulations. An extra EPX formulation was made with half (2%) of the normal Gantrez level at pH of 4.5. The same wipe and pouch and the same loading amount as used in Example 4 were used in this example. Tables 13 and 14 show the ES and EPX formulations used for this test. Table 15

TABLE 15

Formulation composition of ES. All levels listed are % w/w.

| | 687/7/1 | 687/7/2 | 687/7/3 | 687/7/4 | 687/7/5 | 687/7/6 |
|---|---|---|---|---|---|---|
| Target pH | 4.0 | 5.0 | 5.4 | 4.0 | 5.0 | 5.4 |
| Buffer Level | 10 mM | 10 mM | 10 mM | 20 mM | 20 mM | 20 mM |
| Glycopyrrolate | 2.00 | 2.00 | 2.00 | 2.00 | 2.00 | 2.00 |
| Water | 39.12 | 39.11 | 39.10 | 39.04 | 39.02 | 39.01 |
| Ethanol | 58.68 | 58.66 | 58.66 | 58.55 | 58.53 | 58.52 |
| Citric acid (anhydrous) | 0.19 | 0.13 | 0.11 | 0.37 | 0.25 | 0.21 |
| Sodium citrate dihydrate | 0.01 | 0.10 | 0.13 | 0.04 | 0.20 | 0.26 |

TABLE 16

Formulation composition of EPX. All levels listed are % w/w.

| | 687/7/7 | 687/7/8 | 687/7/9 | 687/7/10 | 687/7/11 | 687/7/12 | 687/7/13 |
|---|---|---|---|---|---|---|---|
| Target pH | 4.0 | 5.0 | 5.4 | 4.0 | 5.0 | 5.4 | 4.5 |
| Buffer Level | 10 mM | 10 mM | 10 mM | 20 mM | 20 mM | 20 mM | 10 mM |
| Glycopyrrolate | 2.00 | 2.00 | 2.00 | 2.00 | 2.00 | 2.00 | 2.00 |
| Water | 37.42 | 37.40 | 37.38 | 37.34 | 37.30 | 37.28 | 38.21 |
| Ethanol | 56.13 | 56.09 | 56.08 | 56.01 | 55.96 | 55.93 | 59.32 |
| Citric acid (anhydrous) | 0.19 | 0.08 | 0.01 | 0.05 | 0.19 | 0.10 | 0.14 |

TABLE 16-continued

| Formulation composition of EPX. All levels listed are % w/w. | | | | | | | |
|---|---|---|---|---|---|---|---|
| | 687/7/7 | 687/7/8 | 687/7/9 | 687/7/10 | 687/7/11 | 687/7/12 | 687/7/13 |
| Sodium citrate dihydrate | 0.01 | 0.25 | 0.28 | 0.25 | 0.30 | 0.44 | 0.08 |
| Butyl Ester of PVM/MA Copolymer (Gantrez ES-425) | 4.00 | 4.00 | 4.00 | 4.00 | 4.00 | 4.00 | 2.00 |
| PVP | 0.25 | 0.25 | 0.25 | 0.25 | 0.25 | 0.25 | 0.25 |

Pouches for each formulation were stored at 5° C. and 40° C. without humidity control. Time points were scheduled for 1, 2 and 3 months. The results of the glycopyrrolate assay are shown in Table 17 and Table 18.

TABLE 17

Results of Glycopyrrolate assay. First number is the % glycopyrrolate w/w and the second number is the % degradants calculated by area normalization. % Degradant D1 also shown for 2 month and 3 month.

| ES | | | | | | | |
|---|---|---|---|---|---|---|---|
| | Time | 687/7/1 | 687/7/2 | 687/7/3 | 687/7/4 | 687/7/5 | 687/7/6 |
| | Buffer pH | 10 mM 4.0 | 10 mM 5.0 | 10 mM 5.4 | 20 mM 4.0 | 20 mM 5.0 | 20 mM 5.4 |
| Temp | T = 0 | 2.003 <0.1 | 1.989 <0.1 | 2.002 <0.1 | 2.033 <0.1 | 2.045 <0.1 | 2.041 <0.1 |
| 5° C. | 1 mth | 2.015 <0.1 | — | — | — | — | — |
| | 2 mth | — | — | — | 2.028 <0.1 | — | — |
| 40° C. | 1 mth | 2.001 <0.1 | 2.007 0.2 | 2.002 0.5 | 2.031 <0.1 | 2.018 0.2 | 2.022 0.5 |
| | 2 mth | 2.021 <0.1 | 1.989 0.6 | 1.961 1.2 | 1.995 0.1 | 2.018 0.6 | 1.922 1.2 |
| Degradant D1 | 2 mth | <0.1 | 0.48 | 1.07 | 0.13 | 0.52 | 1.02 |
| | 3 mth | 2.016 0.2 | 1.986 0.9 | — | — | — | — |
| Degradant D1 | 3 mth | 0.15 | 0.74 | — | — | — | — |

| EPX | | | | | | | |
|---|---|---|---|---|---|---|---|
| | Time | 687/7/7 | 687/7/8 | 687/7/9 | 687/7/10 | 687/7/11 | 687/7/12 | 687/7/13 |
| | Buffer pH | 10 mM 4.0 | 10 mM 5.0 | 10 mM 5.4 | 20 mM 4.0 | 20 mM 5.0 | 20 mM 5.4 | 10 mM 4.5 |
| Temp | T = 0 | 2.028 <0.1 | 2.012 <0.1 | 2.021 <0.1 | 1.990 <0.1 | 2.031 <0.1 | 2.002 <0.1 | 2.031 <0.1 |
| 5° C. | 1 mth | — | — | — | — | — | — | — |
| | 2 mth | — | — | — | 1.973 <0.1 | — | — | — |
| | 3 mth | — | — | — | 1.997 0.1 | — | — | — |
| 40° C. | 1 mth | 2.030 0.2 | 2.023 0.4 | 1.974 0.6 | 2.019 0.1 | 2.005 0.4 | 2.022 0.5 | 1.996 0.1 |
| | 2 mth | 1.971 0.4 | 1.928 0.8 | 2.002 1.1 | 1.990 0.5 | 1.954 0.9 | 1.975 1.2 | 1.986 0.4 |
| Degradant D1 | 2 mth | 0.31 | 0.74 | 1.03 | 0.39 | 0.83 | 1.17 | 0.35 |
| | 3 mth | 2.030 0.5 | 1.972 1.1 | — | — | — | — | — |
| Degradant D1 | 3 mth | 0.50 | 1.00 | — | — | — | — | — |

TABLE 18

Results of Glycopyrrolate assay, percentage of T = 0 results

ES

| | Time | 687/7/1 | 687/7/2 | 687/7/3 | 687/7/4 | 687/7/5 | 687/7/6 |
|---|---|---|---|---|---|---|---|
| | Buffer pH | 10 mM 4.0 | 10 mM 5.0 | 10 mM 5.4 | 20 mM 4.0 | 20 mM 5.0 | 20 mM 5.4 |
| 5° C. | 1 mth | 100.6 | — | — | — | — | — |
| | 2 mth | — | — | — | 99.8 | — | — |
| 40° C. | 1 mth | 99.9 | 100.9 | 100.0 | 99.9 | 98.7 | 99.1 |
| | 2 mth | 100.9 | 100.0 | 98.0 | 99.8 | 98.7 | 94.2 |
| | 3 mth | 100.6 | 99.8 | — | — | — | — |

EPX

| | Time | 687/7/7 | 687/7/8 | 687/7/9 | 687/7/10 | 687/7/11 | 687/7/12 | 687/7/13 |
|---|---|---|---|---|---|---|---|---|
| | Buffer pH | 10 mM 4.0 | 10 mM 5.0 | 10 mM 5.4 | 20 mM 4.0 | 20 mM 5.0 | 20 mM 5.4 | 10 mM 4.5 |
| 5° C. | 1 mth | — | — | — | — | — | — | — |
| | 2 mth | — | — | — | 99.1 | — | — | — |
| | 3 mth | — | — | — | 98.5 | — | — | — |
| 40° C. | 1 mth | 100.1 | 100.5 | 97.7 | 101.5 | 98.7 | 101.1 | 98.3 |
| | 2 mth | 97.2 | 95.8 | 99.1 | 100.0 | 96.2 | 98.7 | 97.9 |
| | 3 mth | 100.3 | 98.0 | — | — | — | — | — |

In the results, the pH change of the ES was the same regardless of the buffer level. The pH change for EPX was reduced slightly for 20 mM compared to 10 mM buffer. The preferred formulations for ES and EPX were tested at the pH extremes of 4.0 and 5.0 for 3 months at 40° C. No packaging interactions were observed and color change and pH drift were consistent with the target pH 4.5 formulations in Example 4. The glycopyrrolate degradation rate was higher at the high pH, but within limits to support a 2 year shelf life. The formation of the degradant D1 was also higher at the high pH and had reached 1% of the label claim after 3 months at 40° C.

Example 6

Analysis of DH Changes Over Time of Different Formulations of Glycopyrrolate

To analyze changes in the pH of different ethanol solutions and EPX formulations of glycopyrrolate upon storage under various packaging conditions, the pH of different glycopyrrolate formulations was measured over time for either ethanol solutions or EPX formulations stored in glass bottles or in various pouch materials. The results of these analyses are shown below in Tables 17 to 20.

TABLE 19

Ethanol solution formulations of glycopyrrolate stored in glass bottles - pH Data
(All contain 20 mM buffer except 585/29/18 and the citric/tromethamine formulations)

| F# | Buffer Components | Buffer % w/w | Initial** pH | 1 mth 40° C. pH | 2 mth 40° C. pH | 2 mth 25° C. pH | Initial - 2 mth 40° C. |
|---|---|---|---|---|---|---|---|
| 585/29/15 | Phosphoric acid and Sodium phosphate monobasic | 0.14:0.12 | 3.28 | 3.32 | 3.26 | 3.25 | −0.02 |
| 585/29/16 | Phosphoric acid (adjusted with sodium hydroxide) | 0.28:+0.15 | 4.47 | 4.51 | 4.51 | 4.50 | 0.04 |
| 585/29/4 | Citric Acid and Sodium Citrate | 0.32:0.084 | 4.07 | 4.16 | 4.27 | 4.08 | 0.2 |
| 585/29/6 | Citric Acid and Sodium Citrate | 0.19:0.29 | 5.70 | 5.84 | 5.78 | 5.75 | 0.08 |
| 585/29/13 | Citric Acid and Sodium Citrate (buffer precipitated) | 0.054:0.51 | 7.13 | 6.72 | 6.56 | 6.93 | −0.57 |
| 585/29/18 | Citric Acid and Sodium Citrate (Reduced buffer = 10 mM) | 0.024:0.26 | 7.39 | 6.54 | 6.33 | 6.96 | −1.06 |
| 585/29/19 | Citric Acid and Sodium Citrate (EtOH/Water = 40/60) | 0.19:0.29 | 5.24 | 5.29 | 5.28 | 5.26 | 0.04 |
| 585/29/20 | Citric Acid and Sodium Citrate same ratio as F585/29/6 (EtOH/Water = 40/60) | 0.14:0.37 | 5.82 | 5.81 | 5.72 | 5.80 | −0.1 |
| 585/31/3 | Citric Acid and Tromethamine | 0.40:0.10 | 4.02 | 4.15 | 4.15 | — | 0.13 |

TABLE 19-continued

Ethanol solution formulations of glycopyrrolate stored in glass bottles - pH Data
(All contain 20 mM buffer except 585/29/18 and the citric/tromethamine formulations)

| F# | Buffer Components | Buffer % w/w | Initial** pH | 1 mth 40° C. pH | 2 mth 40° C. pH | 2 mth 25° C. pH | Initial - 2 mth 40° C. |
|---|---|---|---|---|---|---|---|
| 585/31/4 | Citric Acid and Tromethamine | 0.25:0.25 | 5.99 | 5.73 | 5.91 | — | −0.08 |
| 585/29/17 | Sodium phosphate monobasic and sodium phosphate dibasic | 0.14:0.0036 | 7.09 | 5.52 | 5.37 | 5.90 | −1.72 |

**Initial pH taken from 1 month 5° C. data

TABLE 20

Ethanol solution formulations of glycopyrrolate packaged in pouches after 2 months at 50° C. - pH data

| F# | Buffer Components | pH | EAA | SURLYN | 2 mil BAREX | LLDPE |
|---|---|---|---|---|---|---|
| 585/29/4 595/6/1 | Citric Acid and Sodium Citrate | 4.07 4.02 | 4.43 | 4.58 | 4.39 | 4.39 |
| 585/29/6 595/6/2 | Citric Acid and Sodium Citrate | 5.70 5.65 | 5.76 | 5.71 | 5.75 | 5.71 |
| 595/6/5 | Citric Acid and Sodium Citrate (EtOH/Water = 40/60) | 5.26 | 5.33 | 5.42 | 5.32 | 5.29 |
| 595/6/6 | Citric Acid and Sodium Citrate (EtOH/Water = 40/60) | 5.67 | 5.52 | 5.56 | 5.55 | 5.53 |

TABLE 21

EPX formulations of glycopyrrolate stored in glass bottles - pH Data

| F# | Buffer Components | Buffer % w/w | Initial pH | 1 mth 40° C. pH | 2 mth 40° C. pH | 2 mth 25° C. pH | Initial - 2 mth 40° C. |
|---|---|---|---|---|---|---|---|
| 595/3/1 | Citric Acid and Sodium Citrate | 0.33:0.085 | 3.90 | 3.88 | 3.89 | 3.96 | −0.01 |
| 595/3/2 | Citric Acid and Sodium Citrate | 0.19:0.29 | 5.03 | 4.63 | 4.59 | 4.81 | −0.44 |
| 595/3/3 | Citric Acid and Sodium Citrate (Reduced buffer = 10 mM) | 0.024:0.26 | 5.37 | 4.75 | 4.67 | 4.95 | −0.70 |
| 595/3/9 | Citric Acid and Tromethamine (Placebo) | 0.20:0.30 | 5.50 | 4.99 | 4.94 | 5.17 | −0.56 |
| 595/3/10 | Citric Acid and Tromethamine | 0.37:0.13 | 4.11 | 4.01 | 3.97 | 4.04 | −0.14 |
| 595/3/11 | Citric Acid and Tromethamine | 0.13:0.37 | 5.51 | 4.89 | 4.84 | 5.14 | −0.65 |
| 595/3/8 | Phosphoric acid (adjusted with sodium hydroxide) | 0.23:+0.18 | 2.97 | 2.94 | 2.98 | 2.96 | 0.01 |
| 595/3/6 | Sodium phosphate monobasic and sodium phosphate dibasic | 0.18:0.0047 | 4.42 | 4.09 | 4.02 | — | −0.40 |
| 595/3/13 | Sodium phosphate monobasic (adjusted with sodium hydroxide) | 0.18:+ | 5.48 | 4.78 | 4.67 | — | −0.81 |
| 595/3/14 | Sodium phosphate monobasic (adjusted with sodium hydroxide) | 0.18:+ | 6.48 | 5.63 | 5.46 | — | −1.02 |
| 595/3/15 | Sodium phosphate monobasic (adjusted with sodium hydroxide) 0.25% PVP | 0.18:+ | 6.48 | 5.66 | 5.43 | — | −1.05 |

TABLE 22

EPX formulations of glycopyrrolate packaged
in pouches after 2 months at 50° C. - pH data

| F# | Buffer Components | pH | EAA | SURLYN | 2 mil BAREX | LLDPE |
|---|---|---|---|---|---|---|
| 595/3/1 | Citric Acid and Sodium Citrate | 3.90 | 3.85 | 3.95 | 3.80 | 3.82 |
| 595/3/2 | Citric Acid and Sodium Citrate | 5.03 | 4.51 | 4.56 | 4.52 | 4.56 |

The data in Tables 17 to 20 indicate that although some pH changes were observed, the pH of 4.5±0.50 targeted would be most preferably suitable for maintaining both the ethanol solution and EPX formulations within a range of pH 4.0 to 5.0, or about 4 to about 5, over a two year shelf life at 25° C., or about 25° C. Furthermore, the pH drift of solutions of glycopyrrolate after 2 months at 50° C. in pouches was consistent with the results for solutions stored in glass bottles after 2 months at 40° C.

Example 7

Analysis of DH Changes Over Time of Different Formulations of Glycopyrrolate

Figure 10:
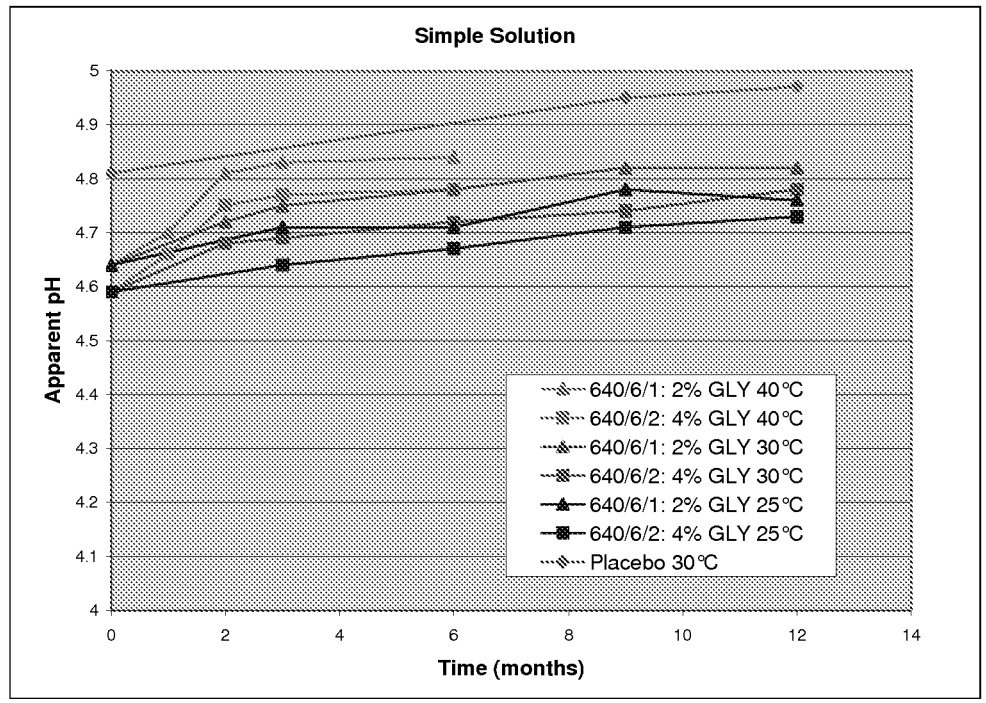
FIG. 10 illustrates an apparent pH of ES and EPX formulations according to Example 7 at 20-25° C.
Figure 10:
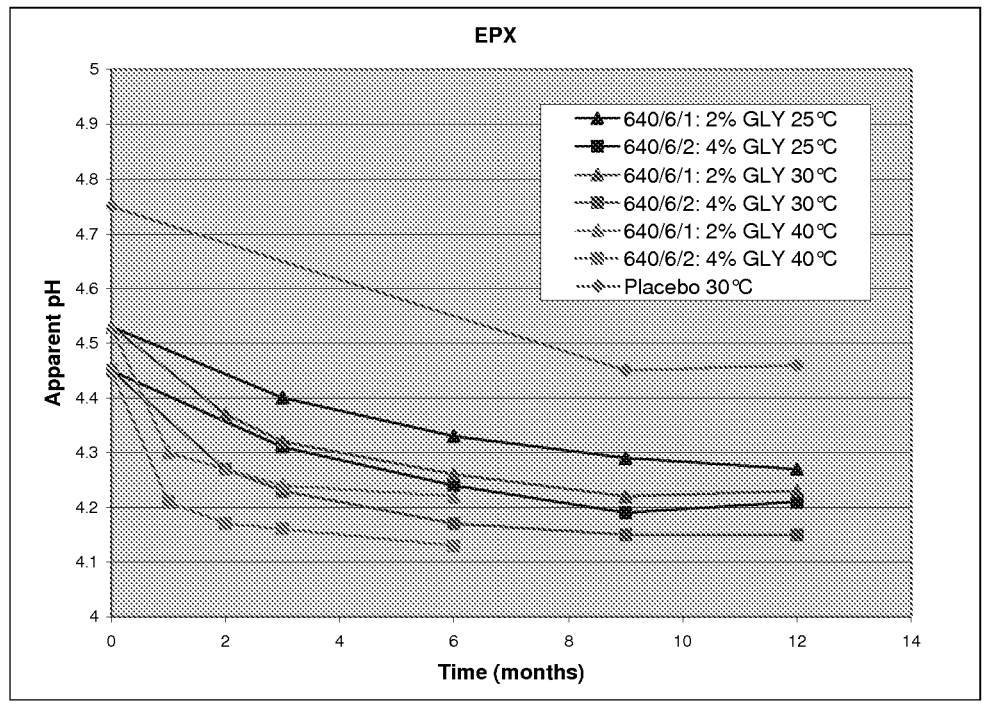

Three wipes containing the formulations of Example 4 were combined and squeezed to collect sufficient wipe solution to test for pH and color change. Approximately 3.5 to 5.0 g was collected. The apparent pH of the ethanol/water solution was measured using a small pH electrode (InLab 423; Mettler-Toledo, Giessen, Germany). The results are shown in FIG. 10 and Table 23. According to these results, the pH change was not excessive.

TABLE 23

Tabulated Results of apparent pH at 20-25° C.

| Temp | Time point (months) | 640/6/1 % w/w | 640/6/2 % w/w | 640/6/4 % w/w | 640/6/5 % w/w |
|---|---|---|---|---|---|
| Bulk Solution | T = 0 | 4.50 | 4.43 | 4.45 | 4.37 |
| Pouches | T = 0 | 4.64 | 4.59 | 4.53 | 4.45 |
| 25° C. | 3 | 4.71 | 4.64 | 4.40 | 4.31 |
| | 6 | 4.71 | 4.67 | 4.33 | 4.24 |
| | 9 | 4.78 | 4.71 | 4.29 | 4.19 |
| | 12 | 4.76 | 4.73 | 4.27 | 4.21 |
| 30° C. | 2 | 4.72 | 4.68 | 4.37 | 4.27 |
| | 3 | 4.75 | 4.69 | 4.32 | 4.23 |
| | 6 | 4.78 | 4.72 | 4.26 | 4.17 |
| | 9 | 4.82 | 4.74 | 4.22 | 4.15 |
| | 12 | 4.82 | 4.78 | 4.23 | 4.15 |
| 40° C. | 1 | 4.70 | 4.66 | 4.30 | 4.21 |
| | 2 | 4.81 | 4.75 | 4.27 | 4.17 |
| | 3 | 4.83 | 4.77 | 4.24 | 4.16 |
| | 6 | 4.84 | 4.78 | 4.22 | 4.13 |

Placebos at T = 0
640/6/3 Bulk solution = 4.73
Pouch = 4.81
640/6/6 Bulk solution = 4.71
Pouch = 4.75

The pH of the bulk solutions after manufacture were all within 0.15 of the pH of 4.50. The 4% glycopyrrolate formulations were slightly lower than the 2% glycopyrrolate formulations. After the pouches were filled and sealed, the pH of the wipe solutions (i.e., squeezed from the wipes) was slightly higher than the bulk solution results, 0.14-0.16 increase for the ES and 0.08 increase for the EPX. All results were still within 0.14 of the target pH.

During storage the pH of the ES formulations both increased, while the EPX formulations both decreased. At 40° C. storage, the ES change appeared linear for 2 months, but the rate of change decreased at both the 3 and 6 month time points. The total increase for the ES after 6 months at 40° C. was 0.19-0.20 for the two API levels. A similar pattern occurred at 25° C. and 30° C., with little change in the pH from the 9 to 12 month time points.

The EPX formulations decreased a greater amount over the first month at 40° C., but the change after 1 month continued to decrease. The total decrease for the EPX over 6 months at 40° C. was 0.31-0.32 for the two glycopyrrolate levels. A similar pattern occurred at 25° C. and 30° C., with no change in the pH from the 9 to 12 month time points. FIG. 10 and Table 23 shows the results of apparent pH at 20-25° C., which indicate that the pH change does not appear to be excessive and the rate of pH change decreases over time.

Example 8

Analysis of the Suitability of Packaging Materials

To assess the suitability of different pouch materials for the packaging of ethanol solution and EPX formulations of glycopyrrolate, either ethanol solutions or EPX formulations were packaged in five pouch materials as indicated in Table 24. 2 to 3 pouches were made for each formulation and pouch material. The pouches were stored at 50° C. Weight loss was measured at 1 and 2 months. At various time points, selected pouches were opened and also assessed for packaging interactions.

TABLE 24

Weight loss data for different pouch materials

| Buffer | Lining | n | 2 month Weight Loss (g) | Lower 95% confidence | Upper 95% confidence |
|---|---|---|---|---|---|
| Citric/Tromethamine | 2 mil Barex | 15 | 0.0026 | 0.0024 | 0.0027 |
| Citric/Tromethamine | 3.5 mil Barex | 12 | 0.0031 | 0.0029 | 0.0034 |
| Citric/Tromethamine | EAA | 9 | 0.0043 | 0.0021 | 0.0064 |
| Citric/Tromethamine | LLDPE | 15 | 0.0020 | 0.0018 | 0.0021 |
| Citric/Tromethamine | Surlyn | 10 | 0.0080 | 0.0038 | 0.0123 |
| Citric/citrate | 2 mil Barex | 22 | 0.0026 | 0.0025 | 0.0028 |
| Citric/citrate | 3.5 mil Barex | 18 | 0.0032 | 0.0030 | 0.0034 |
| Citric/citrate | EAA | 15 | 0.0049 | 0.0030 | 0.0068 |
| Citric/citrate | LLDPE | 25 | 0.0019 | 0.0018 | 0.0020 |
| Citric/citrate | Surlyn | 13 | 0.0047 | 0.0034 | 0.0061 |
| Phosphate | 2 mil Barex | 19 | 0.0026 | 0.0025 | 0.0028 |
| Phosphate | 3.5 mil Barex | 16 | 0.0032 | 0.0029 | 0.0035 |
| Phosphate | EAA | 18 | 0.0143 | 0.0016 | 0.0270 |
| Phosphate | LLDPE | 19 | 0.0020 | 0.0019 | 0.0021 |
| Phosphate | Surlyn | 15 | 0.0822 | −0.0101 | 0.1744 |

Note:
EAA: Ethylene acrylic acid copolymer,
Surlyn: Random copolymer poly(ethylene-co-methacrylic acid) (DuPont),
Barex: Acrylonitrile-methyl acrylate copolymer The data in Table 24 indicates that formulations packaged in LLDPE pouches showed the lowest weight loss, with a very low standard deviation over all LLDPE pouches. Additionally, LLDPE was the only material that had no visible physical interactions (FIG. 1, left hand side representation).

Both the SURLYN and EAA lined pouches showed visible leaking of the formulation between the outer linings of the pouches, and the measured weight loss was higher than with the other linings. The wide range of weight loss data, with several high outliers (more at 2 months than 1 month), also suggested that the formulations were breaking through the lining. One Surlyn pouch had leakage of the formulation completely through the pouch lining. Some small corrosion marks were visible on the lining or some pouches.

The 2 mil BAREX lined pouches showed the second lowest average weight loss. The low standard deviation suggests that the formulation had not broken through the internal Barex layer. The internal Barex lining was cloudy for both the ethanol solution and EPX formulations (FIG. 1, middle representation). De-lamination had also occurred between the Barex and the foil layers for the EPX formulations (FIG. 1, right hand side representation), but not in the case of the ethanol solutions. No other interactions were visible.

The 3.5 mil BAREX lined pouches yielded results similar to those obtained with 2 mil Barex, but the weight loss was slightly higher. This may indicate that the weight loss was occurring at the edges of the pouches, through leakage in the Barex seals rather than in the laminated foil sheets. Because the 3.5 mil Barex would have a thicker seal than the 2 mil Barex, this parameter would provide a larger opening for weight loss to occur.

The data presented in Table 24 indicates that LLDPE would be a desirable material to serve as a pouch lining for the individually packaged glycopyrrolate wipes of the present invention.

Example 9

Preparation of wipes containing Glycopyrrolate formulations

In order to investigate conditions suitable for the preparation of wipes containing glycopyrrolate formulations, 6"×4" and 4"×4" wipes were dosed with 40% to 70% of full capacity with a simple placebo solution and placed into pouches. Pouches were opened over a time period of 16 hours to 40 days, and the amount of wet area was determined. Table 25 below shows the percent area covered when different doses of full capacity were applied to wipes of the indicated dimensions with no applied pressure to the pouch.

TABLE 25

| Area covered | 40% Loading | 50% Loading | 60% Loading | 70% Loading |
|---|---|---|---|---|
| 6" × 4" | 50% | 60% | 68% | 79% |
| 4" × 4" | — | 59% | 66% | 79% |

The data from Table 25 indicates that no wipe was found to have 100% coverage by any applied dose. However, an increased loading level resulted in an increased area covered, and the wipe size had no effect on the percent area covered. Although not indicated by the data in Table 25, no increase in area covered was observed over time. However, application of pressure (e.g., pressing the wipe within the pouch) after sealing resulted in immediate 100% coverage of wipes as shown in FIG. 2. The data in FIG. 2A shows that even after 40 days of storage, a 60% load did not result in complete coverage of the wipe; in contrast, one obtains nearly 100% coverage using a 60% load immediately after application of pressure to a pouch (FIG. 2B).

Example 10

Microbial Limits Test (MLT) and Antimicrobial Effectiveness Test (AET)

At T=0, an AET (BP and USP requirements) and MLT (USP requirements) was performed. The MLT was performed on the final pouch samples. All measurements were <10 or not detected as shown in Table 26.

The AET requires 200 g of formulation, which was impossible to obtain from squeezing the solution from the final pouches. Therefore, the AET was performed on the bulk solution. All results were <10 counts at all time points as shown in Table 26. These results are as expected for the formulations containing over 50% ethanol.

As the formulations are composed of a 60:40 ethanol water base they are not expected to support microbial growth. Furthermore, the formulations are packed in sealed single use pouches. Therefore, further AET and MLT testing was not conducted.

TABLE 26

MLT performed on the final pouch samples

| EML S/No 243807 | Sample Marking: Samples tested as received into the laboratory | Total Viable Aerobic Count (USP)/gm | Pseudo- monas aeruginosa (USP)/ 10 gm | S. aureus (USP)/ 10 gm | Pseudo- monas spp/ 10 gm |
|---|---|---|---|---|---|
| 1 | Lot No 640/6/1 T = 0 | <10 | N/D | N/D | N/D |
| 2 | Lot No 640/6/2 T = 0 | <10 | N/D | N/D | N/D |
| 3 | Lot No 640/6/4 T = 0 | <10 | N/D | N/D | N/D |
| 4 | Lot No 640/6/5 T = 0 | <10 | N/D | N/D | N/D |
| | Method: | 3.1.27 | 3.10.35 | 3.4.21 | 3.10.1.6 |

< = Less than

~ = Estimated

Pres = Presumptive

Y = Yeasts

M = Molds

SPC = Standard Place Count

N/D = Not detected

— = Not tested

TABLE 27

AET on the bulk solutions

Formulation No. 640/6/1

| EML S/No 243814 | Sample Marking: | *Aspergillus niger* cfu/gm | *Candida albicans* cfu/gm | *Pseudomonas aeruginosa* cfu/gm | *Staphylococcus aureus* cfu/gm | *Escherichia coli* cfu/gm |
|---|---|---|---|---|---|---|
| 1 | Initial Challenge | 190000 | 330000 | 400000 | 990000 | 530000 |
| 2 | 48 Hours | — | — | <10 | <10 | <10 |
| 3 | 7 Days | — | — | <10 | <10 | <10 |
| 4 | 14 Days | <10 | <10 | <10 | <10 | <10 |
| 5 | 28 Days | <10 | <10 | <10 | <10 | <10 |
|  | Method: | 3.38.3.1 | 3.38.3.3 | 3.38.3.4 | 3.38.3.4 | 3.38.3.5 |

Formulation No. 640/6/2

| EML S/No 243931 | Sample Marking: | *Aspergillus niger* cfu/gm | *Candida albicans* cfu/gm | *Pseudomonas aeruginosa* cfu/gm | *Staphylococcus aureus* cfu/gm | *Escherichia coli* cfu/gm |
|---|---|---|---|---|---|---|
| 1 | Initial Challenge | 190000 | 330000 | 400000 | 490000 | 530000 |
| 2 | 48 Hours | — | — | <10 | <10 | — |
| 3 | 7 Days | — | — | <10 | <10 | — |
| 4 | 14 Days | <10 | <10 | <10 | <10 | <10 |
| 5 | 28 Days | <10 | <10 | <10 | <10 | <10 |
|  | Method: | 3.38.3.1 | 3.38.3.3 | 3.38.3.4 | 3.38.3.4 | 3.38.3.5 |

Formulation No. 640/6/4

| EML S/No 243933 | Sample Marking: | *Aspergillus niger* cfu/gm | *Candida albicans* cfu/gm | *Pseudomonas aeruginosa* cfu/gm | *Staphylococcus aureus* cfu/gm | *Escherichia coli* cfu/gm |
|---|---|---|---|---|---|---|
| 1 | Initial Challenge | 190000 | 330000 | 400000 | 490000 | 530000 |
| 2 | 48 Hours | — | — | <10 | <10 | — |
| 3 | 7 Days | — | — | <10 | <10 | — |
| 4 | 14 Days | <10 | <10 | <10 | <10 | <10 |
| 5 | 28 Days | <10 | <10 | <10 | <10 | <10 |
|  | Method: | 3.38.2 & 3 | 3.38.2 & 3 | 3.38.2 & 3 | 3.38.2 & 3 | 3.38.2 & 3 |

Formulation No. 640/6/5

| EML S/No 243935 | Sample Marking: | *Aspergillus niger* cfu/gm | *Candida albicans* cfu/gm | *Pseudomonas aeruginosa* cfu/gm | *Staphylococcus aureus* cfu/gm | *Escherichia coli* cfu/gm |
|---|---|---|---|---|---|---|
| 1 | Initial Challenge | 190000 | 330000 | 400000 | 490000 | 530000 |
| 2 | 48 Hours | — | — | <10 | <10 | — |
| 3 | 7 Days | — | — | <10 | <10 | — |
| 4 | 14 Days | <10 | <10 | <10 | <10 | <10 |
| 5 | 28 Days | <10 | <10 | <10 | <10 | <10 |
|  | Method: | 3.38.2 & 3 | 3.38.2 & 3 | 3.38.2 & 3 | 3.38.2 & 3 | 3.38.2 & 3 |

< = Less than
~ = Estimated
Pres = Presumptive
Y = Yeasts
M = Moulds
SPC = Standard Plate Count
N/D = Not detected
— = Not tested Example 11

Measurement of Dose Delivery from Wipes

A. Dose Delivery with 6"×4" and 4"×4" Wipes

Figure 3:
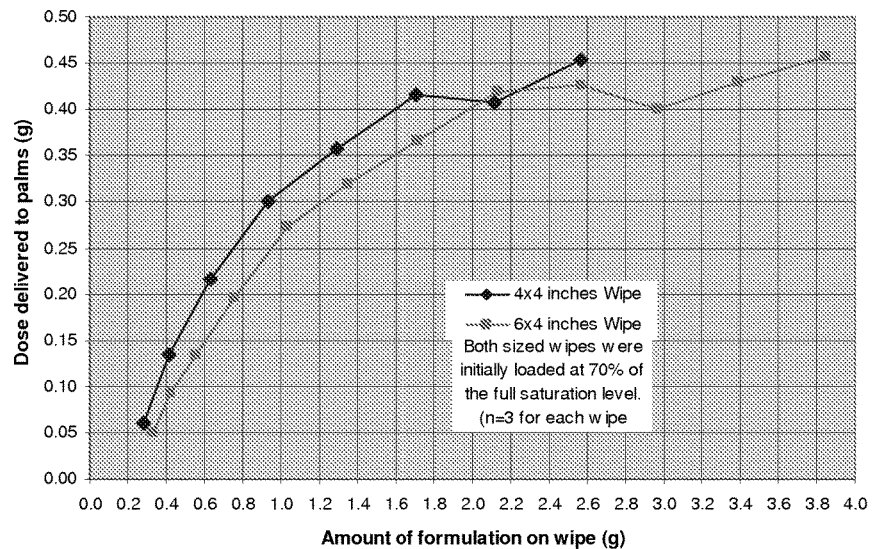
FIG. 3 illustrates the dose delivered to palms as a function of the amount of formulation on a wipe for two different wipe sizes. In particular.
Figure 3:
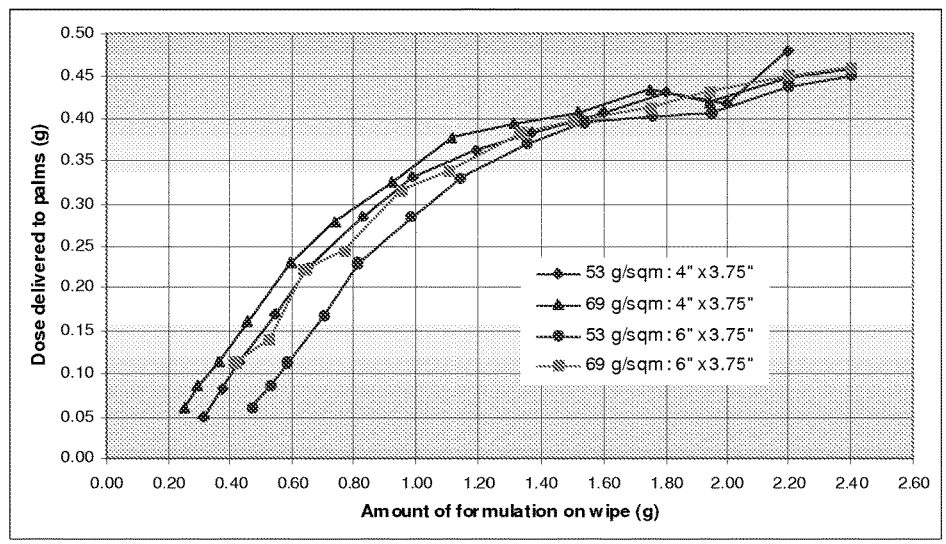

To ascertain the characteristics of dose delivery from wipes of different dimensions that contained varying amounts of glycopyrrolate formulations on wipes, two wipe sizes (6"×4" and 4"×4") were loaded to 70% of capacity, and weight loss from the wipes was measured after repeated wiping onto dry palms. The target area used in these experiments was 320 $cm^2$. FIG. 3 shows the dose delivered to palms as a function of the amount of formulation on a wipe. The data shown in FIG. 3A indicates that the dose delivered by each size of wipe reached a constant level after the amount of formulation on the wipe reached a critical level. In the case of the 4"×4" wipe, this critical level was 1.60 g, and for the 6"×4" wipe, this level was 2.00 g. The dose delivered to the palm at these critical levels of formulation on the wipes was found to be 0.43 g. These data indicate that wipe size and loading amount will not affect the dose delivered, provided that the loading amount is above the critical level for a particular wipe size. Furthermore, partial coverage of a wipe due to incomplete wicking should not affect the dose delivered, although as indicated in Example 6, 100% coverage can be obtained by application of pressure to pouches containing wipes.

B. Dose Delivery with 6"×3.75" and 4"×3.75" Thin (53 g/m$^2$) and Thick (69 g/m$^2$) Wipes Four wipes with different size and thickness were initially loaded with 2.40 g of formulation. The pouch was opened and applied to the palms of both hands of approximately 320 cm$^2$ and the amount lost from the wipe was recorded. After the hands were dried, the same wipe was reapplied to the hands and the dose delivered was recorded. The initial dose delivered to the palms was approximately 0.45 g, leaving 1.95 g on the wipe. This then became the loading amount for the next application. The wipe was continually re-applied until the dose was down to 0.10 g. By subtracting the dose delivered from the amount of formulation remaining on the wipe at each application, a dose versus loading level curve was generated. This curve is shown in FIG. 3B.

Using a single starting loading level of 2.40 g meant the data points were widely spread when there was a large level of formulation on the wipe. Therefore, extra data points were obtained by starting a new wipe with an initial loading of 2.20 g and combining the data into one curve. Each wipe/dose combination had at least 4 replicates. ES placebo was used for the main data to prevent EPX build-up interfering with results, requiring constant rewashing of the hands. The delivery of EPX placebo was checked on 6"×3.75" and 4"×3.75", 69 g/m$^2$ wipes with an initial 2.40 g loading (in duplicate). The EPX dosing results were equivalent to the ES data.

Some initial loadings>2.40 g were also examined. At higher loadings the thicker wipe was the same as shown above, but the thinner wipes felt very wet, and dosing to the hands was slightly higher, approaching 0.50 g.

53 g/m2 4"×3.75" loaded to 2.2 g=0.48 g dose
53 g/m2 6"×3.75" loaded to 3.2 g=0.48 g dose (c.f. 3.0 g loading=0.43 g dose)
69 g/m2 4"×3.75" loaded to 3.0 g=0.44 g dose
69 g/m2 6"×3.75" loaded to 3.3 to 3.5 g=0.41 to 0.43 g (not overly wet).

From the curve in FIG. 3B, it can be seen that the thinner (53 g/m$^2$) wipe has no advantage over the thicker (69 g/m$^2$) wipe that was used in the POC study, the dose delivered is relatively constant at 0.40 to 0.45 g as long as the amount on the wipe was ≥1.5 g, below 1.5 g on the wipe the dose delivered reduced rapidly, the 6×3.75" wipe requires about 0.2 g more on the wipe than the 4×3.75" to deliver above 0.40 g. Accordingly, recommended loading levels to comfortably deliver the maximum dose to an area twice the size of two palms are:

6×3.75"=2.60 g (minimum 2.15 g)
4×3.75"=2.40 g (minimum 1.95 g)
Alternate 5×3.75"=2.50 g Example 12

Measurement of Skin Penetration of Glycopyrrolate Formulations

Figure 4:
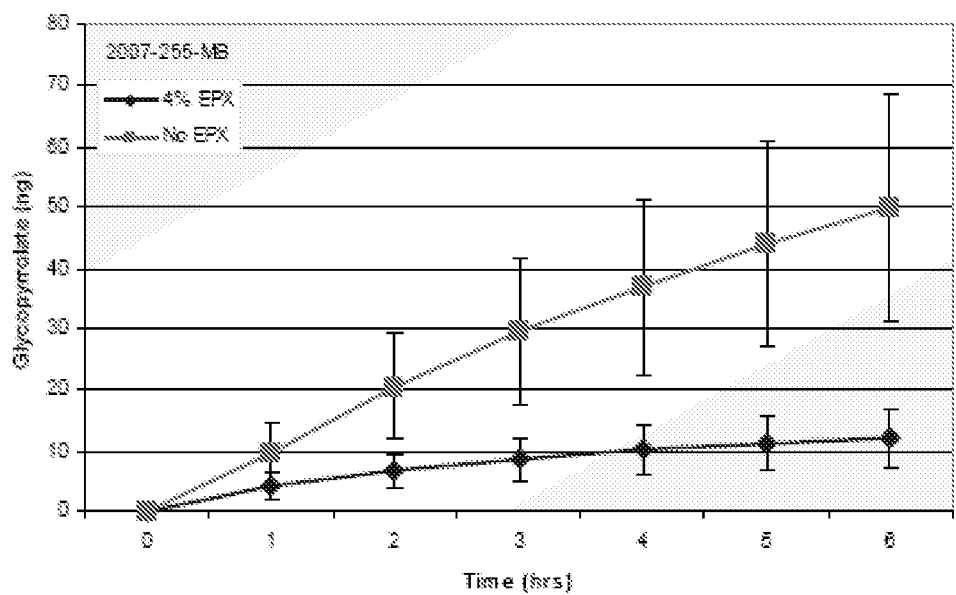
FIG. 4 illustrates skin penetration of glycopyrrolate into the receiving medium through split-thickness skin. Data points represent the average amount of glycopyrrolate (n=7).

Skin penetration tests were conducted to evaluate the difference between formulations comprising EPX polymers and those without. A dose of 5 μl formulation containing 2% glycopyrrolate, 4% propylene glycol, with and without 4% EPX was applied to split-thickness skin (250 μm). The results are shown in FIG. 4.

Example 13

Clinical Trials

With the glycopyrrolate ES and EPX formulations prepared according to the method in Example 1, a clinical trial was conducted in Australia to treat axillary, primary hyperhidrosis in 36 subjects. The treatments and the subjects were as follows.

| Formulation | Glycopyrrolate Content | | |
|---|---|---|---|
| | 0% | 2% | 4% |
| EPX | 6 | 6 | 6 |
| Ethanol Solution | 6 | 6 | 6 |

Each formulations were dosed to the subjects once-daily (QD) in the evenings for 28 days, and they had 6 visits for follow-up at baseline, week 1, week 2, week 3, week 4, and week 6. Hyperhidrosis Disease Severity Scale (HDSS), Gravimetric analysis, Systemic exposure and Adverse events (AEs) were measured. The HDSS score was divided from 1 to 4 depending on the symptom recognition level and for the criteria the score must be 3 or 4.

| Score | Description |
|---|---|
| 1 | My (underarm) sweating is never noticeable and never interferes with my daily activities. |
| 2 | My (underarm) sweating is tolerable but sometimes interferes with my daily activities. |
| 3 | My (underarm) sweating is barely tolerable and frequently interferes with my daily activities. |
| 4 | My (underarm) sweating is intolerable and always interferes with my daily activities. |

For Gravimetric analysis, after drying the axillary surface, a pre-weighed filter paper was applied to the axillary. The paper was covered with plastic wrap (e.g., Saran wrap) and taped around the edges with paper tape. A filter paper was left in contact with the axillary for a period of 5 minutes and then the filter paper was re-weighted. The rate of sweat production was calculated. For the criteria, the filter paper must have at least 50 mg of sweat production in 5 minutes per axilla. Prior axillary use of antiperspirants containing aluminum chloride within 24 hours of study enrollment, glycopyrrolate treatment within 8 weeks, botulinum toxin for axillary hyperhidrosis within 1 year of study enrollment and iontophoresis within 4 weeks study enrollment were excluded in the trial. In addition, concomitant use of antiperspirants were prohibited.

Figure 11:
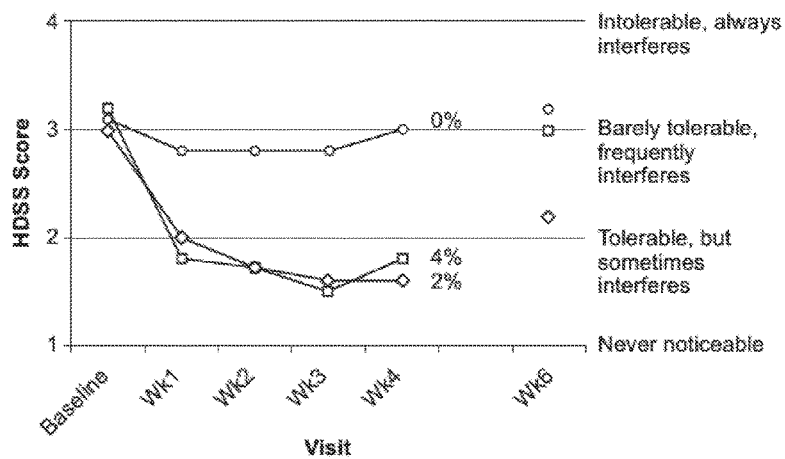
FIG. 11 illustrates the results of clinical trials measured by HDSS for the present ES and EPX formulations. In particular.
Figure 11:
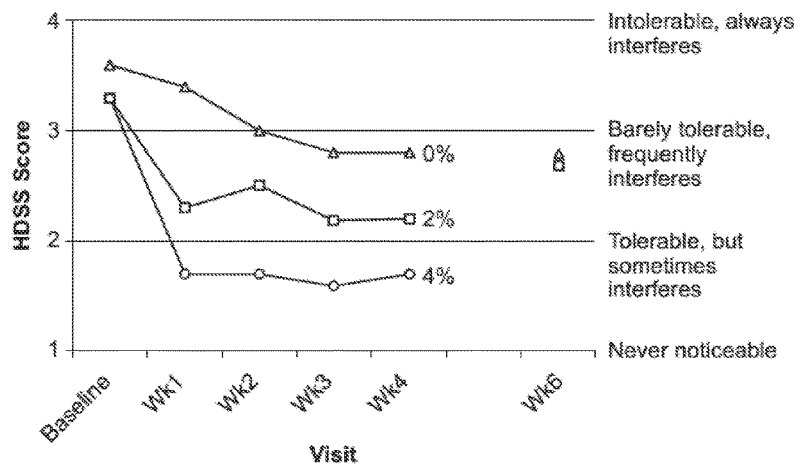
Figure 12:
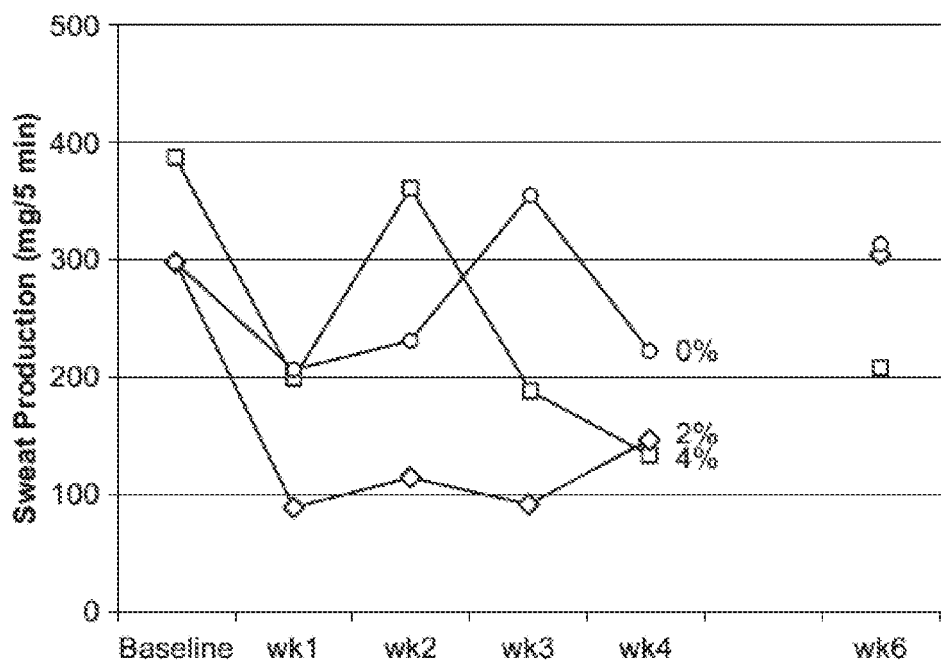
FIG. 12 illustrates the results of clinical trials measured by gravimetric analysis for the present ES and EPX formulations. In particular.
Figure 12:
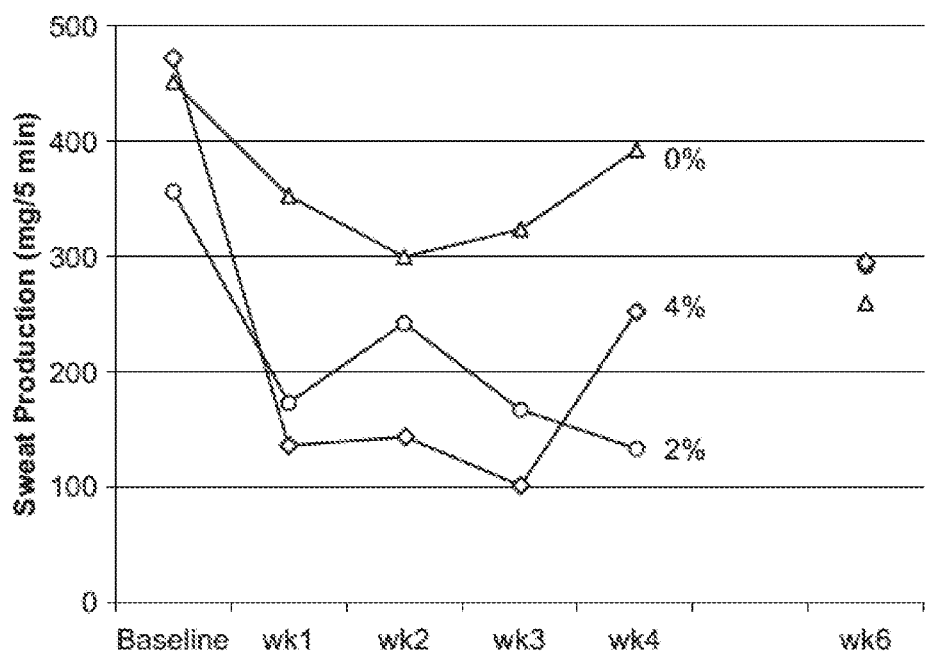

The results from measuring HDSS are shown in FIG. 11. FIG. 11A illustrates average HDSS for the ES formulations. FIG. 11B illustrates average HDSS for the EPX formulations. Also, the results from gravimetric analysis are shown in FIG. 12. FIG. 12A illustrates gravimetric analysis for the ES formulations and FIG. 12B illustrates gravimetric analysis for the EPX formulations. Sweat production was decreased by more than 50% from baseline, measured by gravimetric analysis at week 4. Also, significant improvement of patient quality of life was measured by HDSS. The effect was sustained over 12 weeks. For the safety, Regarding safety, the formulations showed good tolerability with no significant systemic or local side effects. The studied formulations did not occlude the follicular opening and thereby avoided induction of folliculitis. Also, no significant adverse systemic effects seen with the oral anticholinergic therapies, such as dry mouth, blurred vision, urinary retention, or constipation, were observed.

It is understood that the examples and embodiments described herein are for illustrative purposes only and that various modifications or changes in light thereof will be suggested to persons skilled in the art and are to be included within the spirit and purview of this application and scope of the appended claims. All publications, accession numbers, patents, and patent applications cited herein are hereby incorporated by reference in their entirety for all purposes.

What is claimed is:

1. A glycopyrrolate solution comprising:
   about 0.5 to about 4.0% w/w of a glycopyrrolate compound having the following formula:

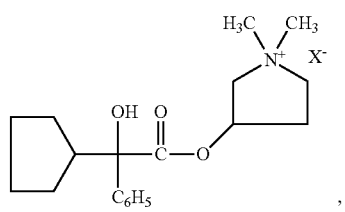

wherein X⁻ is a pharmaceutically acceptable counter ion salt;
   ethanol and water in a weight ratio of about 50:50 to about 60:40;
   a buffering agent, comprising an acid and a base, said acid and base at a total concentration of about 0.2 to about 0.5% w/w and at an acid:base ratio sufficient to maintain a pH of the glycopyrrolate solution of about 3.5 to about 6 at 25° C.;
   wherein the acid is citric acid and the base is selected from the group consisting of sodium citrate and tromethamine;
   wherein the pharmaceutically acceptable counter salt is prepared from an inorganic or organic acid selected from hydrochloric acid, hydrobromic acid, hydrogen fluoride, hydrogen iodide, sulfuric acid, nitric acid, phosphoric acid, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, and salicylic acid.

2. The glycopyrrolate solution of claim 1, wherein the buffering agent maintains a pH of the solution of about 4 to about 5.

3. The glycopyrrolate solution of claim 1, wherein the buffering agent maintains a pH of the solution of about 4.5.

4. The glycopyrrolate solution of claim 1, wherein the glycopyrrolate compound degrades by less than 1% when stored at 0 to 25° C. for at least one month, two months, six months or one year.

5. The glycopyrrolate solution of claim 1, wherein the ethanol to water weight ratio is about 60:40.

6. The glycopyrrolate solution of claim 1, wherein the ethanol is at about 53.7 to about 57.3% w/w, and the water is added to 100% w/w.

7. The glycopyrrolate solution of claim 1, wherein the pharmaceutically acceptable counter salt is prepared from hydrobromic acid.

8. The glycopyrrolate solution of claim 1, wherein the pharmaceutically acceptable counter salt is prepared from p-toluene-sulfonic acid.

9. The glycopyrrolate solution of claim 1, wherein the glycopyrrolate compound is about 2.0% w/w of the glycopyrrolate solution.

10. The glycopyrrolate solution of claim 1, wherein the glycopyrrolate compound is about 4.0% w/w of the glycopyrrolate solution.

11. The glycopyrrolate solution of claim 1, wherein the base is tromethamine.

12. The glycopyrrolate solution of claim 1, wherein the base is sodium citrate.

13. The glycopyrrolate solution of claim 1, further comprising propylene glycol.

14. The glycopyrrolate solution of claim 1, further comprising a polymer system comprising a hydrophobic polymer in combination with a hydrophilic polymer.

15. The glycopyrrolate solution of claim 14, wherein the polymer system comprises a polyvinyl pyrrolidone and a butyl ester of polyvinylmethylether/maleic anhydride copolymer.

16. An individually packaged wipe for the treatment of hyperhidrosis comprising a wipe loaded with the glycopyrrolate solution of claim 1 contained within a pouch resistant to leakage.

17. The individually packaged wipe of claim 16, wherein the wipe is selected from the group consisting of nonwoven material, paper material, woven material, knitted material, tufted material, stitched-bonded material, and material felted by wet-milling material.

18. The individually packaged wipe of claim 16, wherein the pouch comprises an inner lining of linear low density polyethylene (LLDPE).

19. A method for alleviating hyperhidrosis in a mammal comprising the topical administration of the glycopyrrolate solution of claim 1 to an area of the body such that the hyperhidrosis is reduced.

20. A method for alleviating hyperhidrosis in a mammal comprising the topical administration of the wipe of claim 16, following removal from the pouch, to an area of the body such that the hyperhidrosis is reduced.

* * * * *